(12) United States Patent
Nelson et al.

(10) Patent No.: US 12,005,193 B2
(45) Date of Patent: Jun. 11, 2024

(54) CONDUIT CONNECTOR ASSEMBLY OF A PATIENT INTERFACE, AN ANTI-ASPHYXIA VALVE FOR A CONDUIT CONNECTOR ASSEMBLY AND A CONNECTOR

(71) Applicant: Fisher & Paykel Healthcare Limited, Auckland (NZ)

(72) Inventors: Grant Leigh Nelson, Auckland (NZ); Carsten Ma On Wong Corazza, Auckland (NZ); Erik Robertus Scheirlinck, Auckland (NZ); Jae Yun Lim, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1055 days.

(21) Appl. No.: 16/605,634

(22) PCT Filed: May 1, 2018

(86) PCT No.: PCT/NZ2018/050060
§ 371 (c)(1),
(2) Date: Oct. 16, 2019

(87) PCT Pub. No.: WO2018/203759
PCT Pub. Date: Nov. 8, 2018

(65) Prior Publication Data
US 2020/0129724 A1    Apr. 30, 2020

Related U.S. Application Data

(60) Provisional application No. 62/492,750, filed on May 1, 2017.

(51) Int. Cl.
*A61M 16/08* (2006.01)
*A61M 16/06* (2006.01)
*A61M 16/20* (2006.01)

(52) U.S. Cl.
CPC .... *A61M 16/0875* (2013.01); *A61M 16/0616* (2014.02); *A61M 16/0816* (2013.01); *A61M 16/208* (2013.01)

(58) Field of Classification Search
CPC ........... A61B 5/0876; A61M 16/0057; A61M 16/0066; A61M 16/06; A61M 16/0616;
(Continued)

(56) References Cited

U.S. PATENT DOCUMENTS 5,438,981 A * 8/1995 Starr ..................... A62B 7/12
                                                        128/205.24
5,738,087 A    4/1998 King
(Continued)

FOREIGN PATENT DOCUMENTS

GB          799225      8/1958
WO    WO 2010/067237   6/2010
(Continued)

OTHER PUBLICATIONS

International Search Report; PCT/NZ2018/050060; dated Aug. 28, 2018; 7 pages.

*Primary Examiner* — Annette Dixon
(74) *Attorney, Agent, or Firm* — Knobbe Martens Olson and Bear, LLP

(57) ABSTRACT

A conduit connector assembly is provided for a respiratory therapy apparatus and configured to connect a patient interface to a gas delivery conduit. The assembly comprises:
  a conduit comprising a first flow port configured to be connected to the patient interface, and a second flow port configured to be connected to the gas delivery conduit, and a supplementary flow port; and
  a first valve port configured to be closed or opened by a valve flap.
The conduit and the valve flap selectively provide an inspiratory flow path from the second flow port of the
(Continued)

conduit to the first flow port of the conduit; and an expiratory flow path from the first flow port of the conduit to the supplementary flow port via the first valve port. A supplementary gas flow path is provided between the first and/or second flow ports and the supplementary flow port via a supplementary valve port.

19 Claims, 47 Drawing Sheets

(58) Field of Classification Search
CPC .......... A61M 16/0622; A61M 16/0633; A61M 16/0638; A61M 16/0666; A61M 16/0683; A61M 16/08; A61M 16/0816; A61M 16/0825; A61M 16/0875; A61M 16/208; A61M 2016/0042; A61M 2202/0085; A61M 2202/0225; A61M 2205/332; A61M 2205/42; A61M 2206/14; A61M 2210/0618; A61M 2230/60; A61M 2230/63; A62B 7/12; G01F 1/28

See application file for complete search history.

(56) References Cited

U.S. PATENT DOCUMENTS

| 6,691,707 | B1* | 2/2004 | Gunaratnam ..... A61M 16/0683 128/207.13 |
| 8,439,035 | B2* | 5/2013 | Dantanarayana .... A61B 5/0876 128/205.24 |
| 2002/0195108 | A1* | 12/2002 | Mittelstadt .............. F16K 15/16 128/206.15 |
| 2003/0005931 | A1* | 1/2003 | D. Jaffre ............. A61M 16/208 128/200.14 |
| 2004/0094157 | A1* | 5/2004 | Dantanarayana .......................... A61M 16/0875 128/207.12 |
| 2009/0065729 | A1 | 3/2009 | Worboys et al. |
| 2009/0272380 | A1 | 11/2009 | Jaffre et al. |
| 2012/0304985 | A1 | 12/2012 | Lalonde |
| 2014/0305431 | A1 | 10/2014 | Holley et al. |
| 2015/0059763 | A1 | 3/2015 | Chien et al. |
| 2016/0184549 | A1* | 6/2016 | Bugamelli ........ A61M 16/0816 137/515 |

FOREIGN PATENT DOCUMENTS

WO   WO 2015/022629   2/2015
WO   WO.2017/021836   2/2017

* cited by examiner

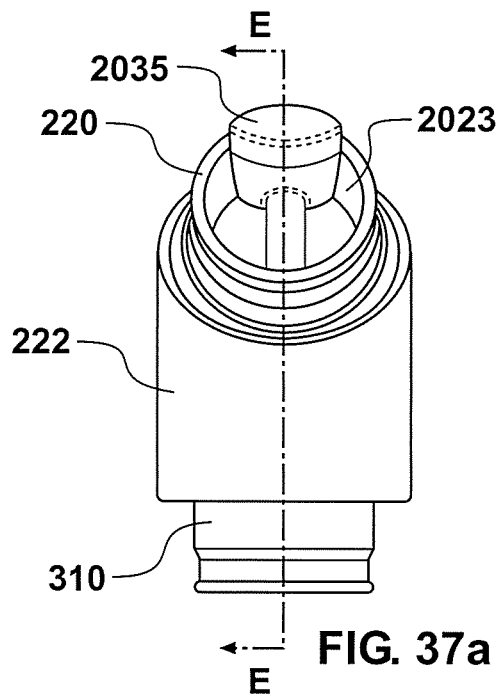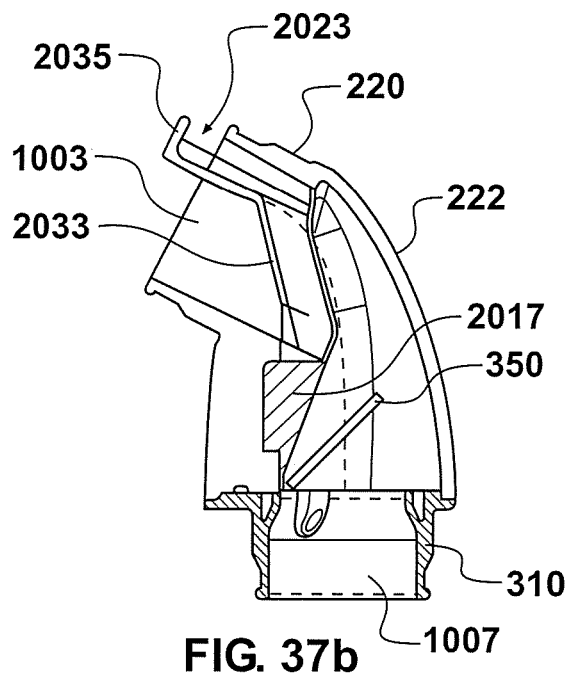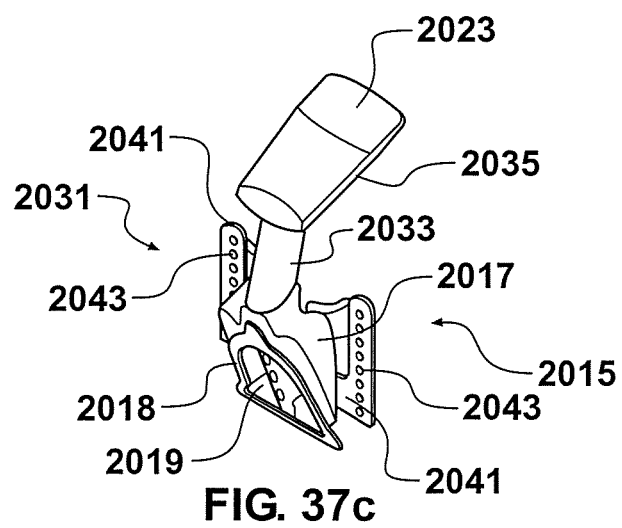

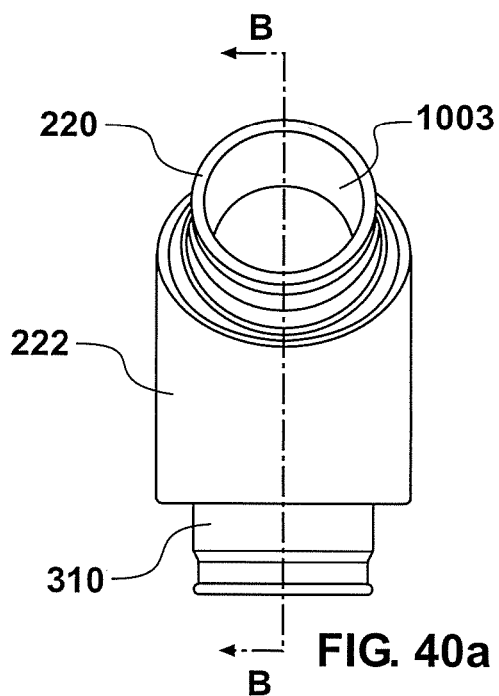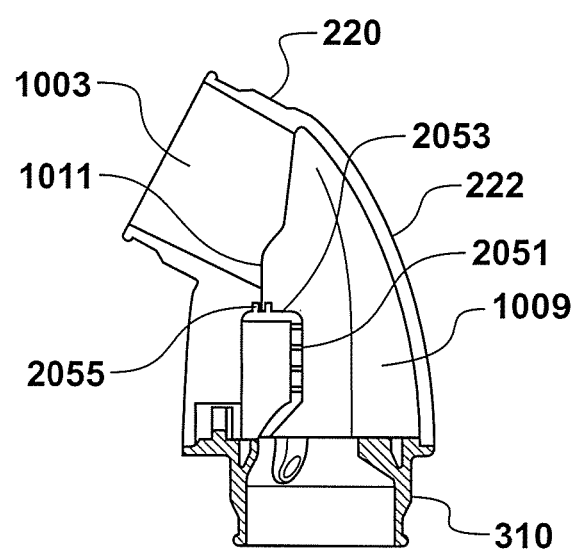
FIG. 40a
FIG. 40b
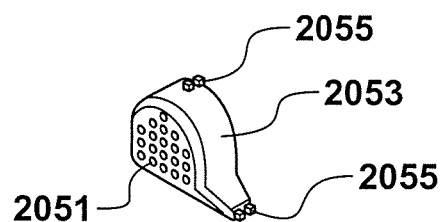
FIG. 40c

CONDUIT CONNECTOR ASSEMBLY OF A PATIENT INTERFACE, AN ANTI-ASPHYXIA VALVE FOR A CONDUIT CONNECTOR ASSEMBLY AND A CONNECTOR

FIELD OF THE DISCLOSURE

The present disclosure generally relates to a conduit connector assembly of a patient interface such as a face mask that covers at least one of a nose and a mouth of a user to supply respiratory gas under positive pressure. More particularly, the present disclosure relates to such conduit connector assemblies that have an anti-asphyxia valve (an AA valve) arranged to enable the user to continue to breathe, if the respiratory gas supply is switched off or stops for any reason. In some examples the conduit connector assembly is an elbow assembly. The disclosure also relates to a connector for connecting a conduit to a patient interface, such as via an elbow assembly, preferably the elbow assemblies disclosed herein.

BACKGROUND

Face masks can be used to provide respiratory gases to a user under positive pressure. In configurations in which both a mouth and a nose of a user are covered, the full face mask typically will overlie a bridge of the nose. Generally, a single seal will circumscribe the nose and the mouth of the user.

Such full face masks commonly are secured to a head of the user with headgear. In order to sufficiently reduce leakage, the headgear typically is tightened, which results in an elevated pressure being exerted on a bridge of a user's nose. In other words, as the headgear is tightened, the seal typically applies a progressively increasing load on the bridge of the nose. Such masks are typically provided with a conduit connector assembly typically comprising a tubular conduit, one end of the conduit being in fluid communication with the mask, the other end of the conduit being connected to a breathing gas delivery tube. Such a conduit connector assembly can comprise an elbow assembly comprising a tubular conduit which includes a bend. In some examples, the bend may extend through 90 degrees. It can be a problem that AA valves in such conduit connector assemblies do not open or close fully or reliably.

SUMMARY OF THE DISCLOSURE

It is an object of the present disclosure to provide one or more constructions and/or methods that will at least go some way towards improving on the above or that will at least provide the public or the medical profession with a useful choice.

According to an aspect of the disclosure there is provided a conduit connector assembly for a respiratory therapy apparatus and configured to connect a patient interface to a gas delivery conduit, the elbow assembly comprising:
  a conduit comprising a first flow port configured to be connected to the patient interface, and a second flow port configured to be connected to the gas delivery conduit, and a supplementary flow port; and
  a hollow valve body configured to be mounted on or in the conduit and comprising at least a first valve port configured to be closed or opened by a valve flap,
  the conduit, valve body and the valve flap being configured to selectively provide two flow paths through the elbow, being:
    an inspiratory flow path from the second flow port of the conduit to the first flow port of the conduit;
    an expiratory flow path from the first flow port of the conduit to the supplementary flow port via the first valve port of the valve body, wherein:
    a supplementary gas flow path is provided between the first and/or second flow ports and the supplementary flow port via a supplementary valve port of the valve body.

According to another aspect of the disclosure there is provided a conduit connector assembly for a respiratory therapy apparatus and configured to connect a patient interface to a gas delivery conduit, the conduit connector assembly comprising:
  a conduit comprising a first flow port configured to be connected to the patient interface, and a second flow port configured to be connected to the gas delivery conduit, the first and second flow ports being in fluid communication via a flow channel extending through the conduit;
  a wall of the conduit comprising an expiratory flow port; and
  a hollow valve body configured to be mounted on or in the conduit and having first and second valve ports, the first valve port being in communication with the interior of the conduit, the second valve port being in communication with first valve port and the expiratory flow port, the first valve port being closable via a valve flap,
  wherein when the valve flap is in a first position, the valve flap at least partially blocks the first valve port and allows gas from the gas delivery conduit to pass to a user via the conduit, and
  when the flap is in a second position, the flap at least partially blocks the gas delivery conduit thereby allowing gas to flow from the user into the valve body via the first valve port and through the expiratory flow port via the second valve port,
  wherein the valve body comprises a supplementary valve port which forms a supplementary gas flow path between the conduit flow channel and the expiratory flow port.

The valve body and/or conduit may be configured such that the supplementary gas flow path is permanently open.

The supplementary valve port may be formed on the valve body.

The supplementary valve port may comprise an array of valve ports formed on the valve body.

The supplementary valve port may be formed on a supplementary gas flow duct in communication with the valve body.

The supplementary valve port may be formed at one end of the supplementary gas flow duct distal from the valve body.

The supplementary gas flow duct may project from the valve body into the conduit. The supplementary gas flow duct may project from the valve body to a position adjacent the first port of the conduit. The supplementary gas flow duct may project from the valve body to a position projecting beyond the first port of the conduit, outside of the conduit.

The supplementary gas flow duct may comprise a relatively narrow diameter portion which extends from the valve body and along the conduit.

The supplementary valve port may be defined in a relatively wide mouth portion of the supplementary gas flow duct, the mouth portion being distal from the valve body.

The valve body may be elongate and comprises first and second end faces, the end faces comprising the first and second valve port respectively. The first end face may be planar, with the plane of the first end face being inclined relative to a longitudinal axis of the valve body. The second end face is planar, with the plane of the first end face being perpendicular to a longitudinal axis of the valve body.

The valve body may comprise a conduit insert mounted or at least located inside the conduit.

The supplementary valve port may comprise a single or a plurality of opening(s).

The valve flap may comprise an elongate bead which projects from the flap and is configured to contact an inner wall of the conduit when the flap is in the first position so as to space the flap from the inner wall of the conduit, the bead comprising at least one tapered portion configured such that part of the bead projects further from the flap than another part of the bead, when the flap is viewed from the side. The bead may extend around at least part of the periphery of the valve flap. The bead may extend around the entire periphery of the valve flap.

The flap may comprise a hinge which pivotally mounts the flap on the elbow, the bead extending around the periphery of the flap to the hinge.

The conduit connector assembly may comprise a diffuser configured to diffuse gas flow through the valve body and/or through the or each supplementary or expiratory flow port. The diffuser may comprise a plurality of flow apertures.

The conduit connector assembly may further comprise a sleeve coupled with the conduit, the sleeve being configured to fluidly couple with the gas delivery conduit.

The valve body may comprise a sub-assembly removably mounted in the conduit.

The supplementary gas flow duct may be elongate and substantially tubular along its length.

The supplementary gas flow duct may extend along more than half the length of the conduit.

The supplementary gas flow duct may comprise a plurality of sub-passages extending along its length. The one or more sub-passage may be inclined relative to another. The one or more sub-passage may have a transverse cross sectional profile that is different to that of another sub-passage. The conduit connector assembly may comprise inlet and outlet sub-passages interconnected by an intermediate sub-passage. The inlet and outlet sub-passages may flare radially outwardly, and the intermediate sub passage may be narrower and substantially tubular.

The supplementary gas flow duct may comprise a relatively short duct positioned inside the conduit and projecting into the conduit. The duct may project across less than half the diameter of the conduit. The end of the duct may project into the conduit is closed by a duct end wall, the duct end wall being provided with at least one orifice configured to allow expiratory gas to flow from the conduit through the orifice and into the duct. The conduit connector assembly may comprise a plurality of orifices.

According to another aspect of this disclosure, there is provided a conduit connector assembly for a respiratory therapy apparatus and configured to connect a patient interface to a gas delivery conduit, the assembly comprising:
 a conduit comprising:
  a first flow port configured to be connected to the patient interface,
  a second flow port configured to be connected to the gas delivery conduit,
  a supplementary flow port; and
  at least a first valve port configured to be closed or opened by a valve flap,
 the conduit and the valve flap being configured to selectively provide two flow paths through the conduit, being:
  an inspiratory flow path from the second flow port of the conduit to the first flow port of the elbow;
  an expiratory flow path from the first flow port of the conduit to the supplementary flow port via the first valve port, wherein:
  a supplementary gas flow path is provided between the first and/or second flow ports and the supplementary flow port via a supplementary valve port defined by, or comprising part of:
  the valve flap; or
  the part of the conduit against which the valve flap seals when the valve flap provides the supplementary gas flow path.

The supplementary valve port may be provided by a flow slot provided on or comprising part of the valve flap.

The slot may extend from a position radially inward of a perimeter of the valve flap to a position at the perimeter of the valve flap, such that the supplementary flow path extends through the perimeter of the valve flap.

A plurality of supplementary valve ports may be provided. The plurality of supplementary valve ports may be equispaced.

The plurality of supplementary valve ports are arranged in a symmetrical formation about a centre axis of the valve flap, when the flap is viewed from above.

The valve flap may comprise a substantially planar face, wherein the or each slot is defined between two upstanding portions of the valve flap that project away from the planar face. The planar face may comprise at least one recessed portion or region, each slot being in fluid communication with a recessed portion or region. A plurality of recessed portions or regions may be provided.

The valve flap may comprise a hinge or pivot about which the valve flap rotates in use, the supplementary valve port(s) being provided at a position distal from the hinge or pivot. The distal position may comprise an arcuate part of a perimeter of the valve flap.

The valve flap may comprise one or more reinforced portions.

The valve flap may comprise a sealing face, the supplementary valve port extending through the sealing face.

The sealing face may be provided about the perimeter of the valve flap.

The sealing face may be tapered, when the valve flap is viewed from the side.

The conduit connector assembly may further comprise a flow restricting formation, configured to prevent or restrict the flow of gas across or along at least part of the valve flap. The conduit may comprise an internal support structure or feature, the flow restricting formation being configured to prevent or restrict the flow of gas into or over the internal support structure or feature.

The conduit connector assembly may comprise an elbow conduit connector assembly, the conduit comprising an elbow conduit.

According to a further aspect of this disclosure there is provided a respiratory therapy system comprising the conduit connector assembly of any one or more of the preceding statements.

The respiratory therapy system may further comprise any one or more of:
 a patient interface;
 a gas delivery conduit;

a headgear configured for mounting the patient interface on the head of a user; and one or more connectors configured to connect the gas delivery conduit and/or the patient interface to the elbow or conduit connector assembly.

The respiratory therapy system may be configured to provide non-invasive ventilation, and be a single limb system comprising, or may be configured to be connected to, a single gas delivery conduit.

According to a further aspect of this disclosure there is provided a connector assembly for a respiratory therapy apparatus and configured to connect a patient interface to a gas delivery conduit, the connector assembly comprising:

an elongate connector comprising a first end and a first flow port configured to be connected to the patient interface, and a second end comprising a second flow port configured to be connected to the gas delivery conduit, the first and second flow ports being in communication via a flow channel extending through the connector;

a wall of the connector comprising an expiratory flow port; wherein the second end is configured to be selectively connectable to at least one of a plurality of different gas flow directing structures, each gas flow directing structure being configured to direct inspiratory and/or expiratory gas through the connector along a predetermined gas flow path associated with the particular gas flow directing structure.

The predetermined gas flow path may comprise any one of:

an inspiratory gas flow path from the second flow port to the first flow port along the flow channel;

an inspiratory gas flow path from the expiratory flow port to the first flow port;

an expiratory gas flow path from the first flow port to the expiratory flow port;

an expiratory gas flow path from the first flow port to a further flow port provided in the gas flow directing structure.

The gas flow directing structure may comprise a supplementary gas flow duct configured to be located in and extend at least partially into the flow channel, the flow duct having a first port open to the flow channel, and a second port, distal from the first port and configured to be in fluid communication with the expiratory flow port.

The supplementary gas flow duct may comprise a hollow body configured to be mounted in the connector in communication with the expiratory flow port, the hollow body projecting into the flow channel of the connector.

The hollow body may comprise a mouth opening configured to deliver inspiratory gas to the patient or to receive expiratory gas from the patient.

The mouth opening may comprise an array of openings.

The hollow body may be elongate and extends along at least part of the flow channel.

The mouth opening may be positioned adjacent the first flow port of the connector.

The hollow body may comprise a cap having a mouth opening which is positioned in the flow channel of the connector, remoted from the first flow port of the connector. The cap may be wedge shaped when viewed from the side, so as to have an inclined face, the mouth opening being provided in the inclined face.

The hollow body may comprise a hollow valve body configured to be mounted on or in the connector and having first and second valve ports, the first valve port being in communication with the interior of the connector, the second valve port being in communication with the first valve port and the expiratory flow port, the first valve port being closable via a valve flap, wherein when the valve flap is in a first position, the valve flap at least partially blocks the first valve port and allows gas from the gas delivery conduit to pass to a user via the connector, and when the flap is in a second position, the flap at least partially blocks the gas delivery conduit thereby allowing gas to flow from the user into the valve body via the first valve port and through the expiratory flow port via the second valve port.

The gas flow directing structure may comprise a valve assembly comprising a valve flap; wherein when the valve flap is in a first position, the valve flap at least partially blocks the first valve port and allows gas from the gas delivery conduit to pass to a user via the connector, and when the flap is in a second position, the flap at least partially blocks the gas delivery conduit thereby allowing gas to flow from the user into the valve body via the first valve port and through the expiratory flow port via the second valve port.

Each gas flow directing structure may be configured to be removably mounted in the second end of the connector assembly.

The connector assembly and/or the gas flow directing structure may be provided with at least one:

guiding formation configured to guide the gas flow directing structure into the connector assembly;

orientating formation configured to correctly orientate the gas flow directing structure into the connector assembly;

locking or clipping or snap-fit formation configured to lock or clip or snap-fit the gas flow directing structure in the connector assembly.

The connector assembly may further comprise a diffuser configured to diffuse the gas flow through the connector. The diffuser may be configured to diffuse gas flow through the expiratory flow port.

The connector may comprise an interior dividing wall, the flow channel being defined on one side of the dividing wall, the dividing wall comprising a valve opening, the valve opening being in fluid communication with a chamber on the other side of the dividing wall from the flow channel, the chamber being in communication with the expiratory flow port; wherein each gas flow directing structure is configured to be mounted on the dividing wall such that the gas flow directing structure is in communication with the valve opening.

The connector assembly may further comprise a swivel connector at one or both of the first and second ends and configured to provide a rotatable connection with the patient interface or gas delivery conduit respectively.

The connector assembly may be an elbow connector assembly and the elongate connector comprises an elbow connector.

According to another aspect of this disclosure there is provided a connector assembly kit comprising:

the connector assembly of any one of the above statements; and a plurality of gas flow directing structures.

According to another aspect of this disclosure there is provided a conduit connector assembly for a respiratory therapy apparatus and configured to connect a patient interface to a gas delivery conduit, the assembly comprising:

a conduit comprising a first flow port configured to be connected to the patient interface, and a second flow port configured to be connected to the gas delivery conduit, and a supplementary flow port; and a first valve port configured to be closed or opened by a valve flap, the conduit and the valve flap being configured to selectively provide two flow paths through the conduit, being:

an inspiratory flow path from the second flow port of the conduit to the first flow port of the conduit;

an expiratory flow path from the first flow port of the conduit to the supplementary flow port via the first valve port, wherein:

a supplementary gas flow path is provided between the first and/or second flow ports and the supplementary flow port via a supplementary valve port.

The supplementary valve port may be provided on, or comprise part of:

the valve flap; or a hollow valve body configured to be mounted on or in the conduit.

According to an aspect of the disclosure there is provided an elbow assembly configured to connect a mask assembly to an air and/or other gases conduit, the elbow assembly comprising:

an elbow and a sleeve, the elbow comprising inner and outer walls and defining an air and/or other gases flow channel therebetween, the inner wall comprising a port on a side of the elbow, the sleeve being coupled with the elbow;

the sleeve comprising a flap, wherein when the flap is at a first position, the flap at least partially blocks the port and allows gas from the conduit to pass to a user via the elbow, and when the flap is at a second position, the flap at least partially blocks the conduit thereby allowing gas to flow from the user to a location outside of the elbow assembly via the port and the flow channel, wherein the flow channel directs air and/or other gases away from the side of the elbow, the flap in some embodiments comprising an elongate bead which projects from the flap and is configured to contact the inner wall of the elbow when the flap is in the first position so as to space the flap from the inner wall of the elbow, the bead comprising at least one tapered portion configured such that part of the bead projects further from the flap than another part of the bead, when the flap is viewed from the side.

In some embodiments, the bead extends around the periphery of the valve flap.

The flap may comprise a hinge which pivotally mounts the flap on the elbow, the bead extending around the periphery of the flap to the hinge.

The bead may comprise an arcuate bead portion distal from the hinge, the bead portion being arcuate when the flap is viewed in plan. The bead may additionally or alternatively comprise at least one linear bead portion adjacent the hinge, the bead portion being straight when the flap is viewed in plan. The linear bead portion may comprise a sealing surface which is wider than the width of the remainder of the bead. The width of the at least one linear bead portion may be substantially identical to a height of a surface of another part of the elbow assembly against which the at least one linear bead portion seals, when the flap is in the first position. A transitional wall may be defined between the at least one linear bead portion and the remainder of the flap, the transitional wall extending from the margin of the linear bead portion to the body of the flap, the transitional wall being configured to provide structural stiffness to the flap. The transitional wall may be inclined relative to the plane of the valve flap. In one example, the bead is substantially 'n' shaped when the flap is viewed in plan. In another example, the bead may be substantially 'D' shaped when the flap is viewed in plan.

The bead may taper inwardly towards the valve flap from a position distal from the hinge to a position adjacent the hinge, that is, the bead projects further from the flap at a position distal from the hinge. The bead may taper such that the bead blends into the valve flap, at a position adjacent the hinge.

The bead preferably comprises a top surface which contacts the inner wall of the elbow when the flap is in the first position, and opposed side walls extending between the valve flap and the top surface. At least one side wall may be curved. At least one side wall may be straight. The profile shape of one side wall may be different from the shape of another side wall. In one example, the profile of one side wall is such that the side wall curves from the top surface into a plane of the valve flap. In one example, at least one side wall is substantially straight in profile so that that side wall extends in a straight line between the top surface and the valve flap. The straight side wall may be inclined relative to the plane of the valve flap.

The bead may be formed integrally with the valve flap. A plurality of beads may be provided.

The flap may comprise a flap support, the flap support being mounted on at least one of the elbow and the sleeve. An orientation feature may be provided and arranged to facilitate mounting the support and the valve flap in the desired orientation relative to the elbow and sleeve. The orientation feature may comprise a slot on one of the support and the elbow or sleeve and a protrusion on the other of the support and the elbow or sleeve, the protrusion being received in the slot when the support and the valve flap are mounted in the desired orientation.

The flow channel may comprise two flow channels.

The sleeve may further comprise a bump extending around an outer surface of the sleeve and a recess adjacent to the bump. The bump and the recess may be adapted to receive a swiveling component incorporating a ridge to engage with the bump.

The flap may be configured such that the flap is biased away from the elbow towards the sleeve, at least when the flap is in the second position. The flap may be configured such that the flap is biased away from the first position, at least when the flap is in the second position. The flap may be biased away from the second position in a direction also away from the first position. The flap may comprise a recess on an opposite face of the flap to the bead. The recess may be oblong. The recess may be adjacent a hinge of the flap.

According to another aspect of the disclosure there is provided an anti-asphyxiation valve for mounting in an elbow assembly configured to connect a mask assembly to an air and/or other gases conduit, the elbow assembly comprising:

an elbow and a sleeve, the elbow comprising inner and outer walls and defining an air and/or other gases flow channel therebetween, the inner wall comprising a port on a side of the elbow, the sleeve being coupled with the elbow;

the valve comprising a support and a flap pivotally mounted on the support, wherein when the valve flap assembly is mounted in an elbow and assembly and when the flap is at a first position, the flap at least partially blocks the port and allows gas from the conduit to pass to a user via the elbow, and when the flap is at a second position, the flap at least partially blocks the conduit thereby allowing gas to flow from the user to a location outside of the elbow assembly via the port and the flow channel, wherein the flow channel directs air and/or other gases away from the side of the elbow, the flap in some embodiments comprising an elongate bead which projects from the flap and is configured to contact the inner wall of the elbow when the flap is in the first position so as to space the flap from the inner wall of the elbow, the bead comprising at least one tapered portion configured such that part of the bead projects further from the flap than another part of the bead, when viewed from the side.

According to another aspect, there is provided a connector for connecting an air and/or other gases conduit, directly or indirectly, to a patient interface, the connector comprising:
a first end and a second end; and
a wall defining a gases pathway between the first end and the second end;
wherein the first end is configured to couple to an elbow connector and the second end is configured to couple to a respiratory gases tube, including via a tube connector, such as a collar, that terminates the respiratory tube, and
further wherein the second end of the connector is configured to prevent fixed attachment of the second end of the connector to the elbow connector.

Preferably, the second end of the connector is dimensioned relative to the elbow connector so as to provide said prevention. More particularly, according to a preferred embodiment, an engaging portion of the elbow connector is configured to be received inside the connector and the inner dimension of the second end is greater than the external dimension of the engaging portion of the elbow connector.

Preferably, the connector is configured to releasably and sealably be secured to the elbow connector via a click or snap fit. To this end, a projection or recess may be provided on a surface (preferably an interior surface) of the connector and the engaging portion of the elbow connector may include a corresponding recess or projection. Thus the disclosure may further provide an elbow connector configured to engage the novel and inventive connector.

According to some embodiments, the connector comprises a projection on an outer surface thereof that is configured to act as a mechanical stop to limit the extent to which a respiratory tube may be pushed onto the connector. The external projection is preferably also configured to provide a grip for a user's fingers for facilitating removal of the connector from the elbow connector. It should be noted that this external projection may be used with or without the connector being configured to prevent engagement of the second end thereof with the engaging portion of the elbow connector (e.g. elbow 29 or 29a).

It will be appreciated that while air may be provided as respiratory assistance, this may be supplemented or replaced with other gases. Additionally or alternatively, medications may be provided to patients, such as via a nebulizer that is coupled to the patient interface or more typically, part of the breathing circuit feeding gases to the patient. As such references to "air" and even "gases" are not to be interpreted narrowly.

BRIEF DESCRIPTION OF THE DRAWINGS

These and other features, aspects and advantages of embodiments of the present disclosure will be described with reference to the following drawings.

FIG. 23c is an alternative perspective view of the connector and elbow assembly of FIG. 23a.

FIGS. 37a-c are, respectively, rear, sectional side and part enlarged views of another configuration of an elbow assembly.

FIGS. 40a-c are, respectively, rear, sectional side and part enlarged views of another configuration of a conduit connector assembly in the form of an elbow assembly.

DETAILED DESCRIPTION OF THE PREFERRED EMBODIMENT

Figure 1:
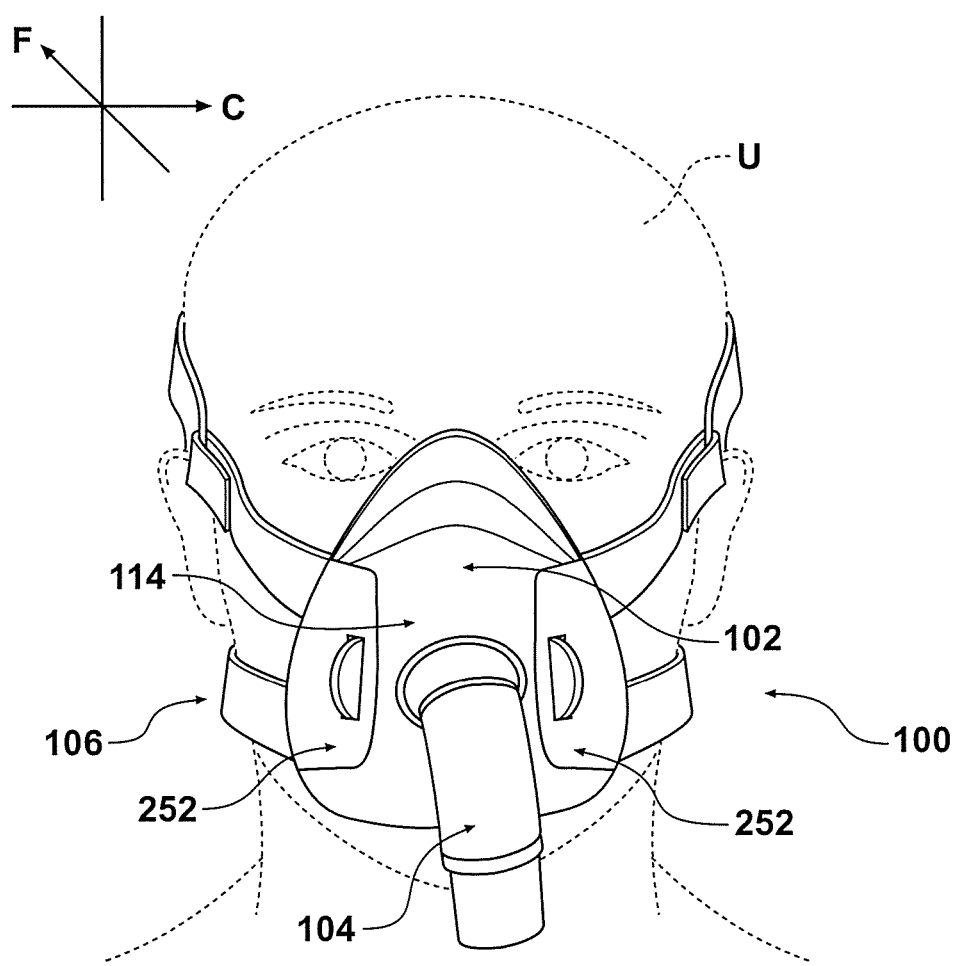
FIG. 1 is front view of a user wearing an interface that is arranged and configured in accordance with certain features, aspects and advantages of the present disclosure.
Figure 2:
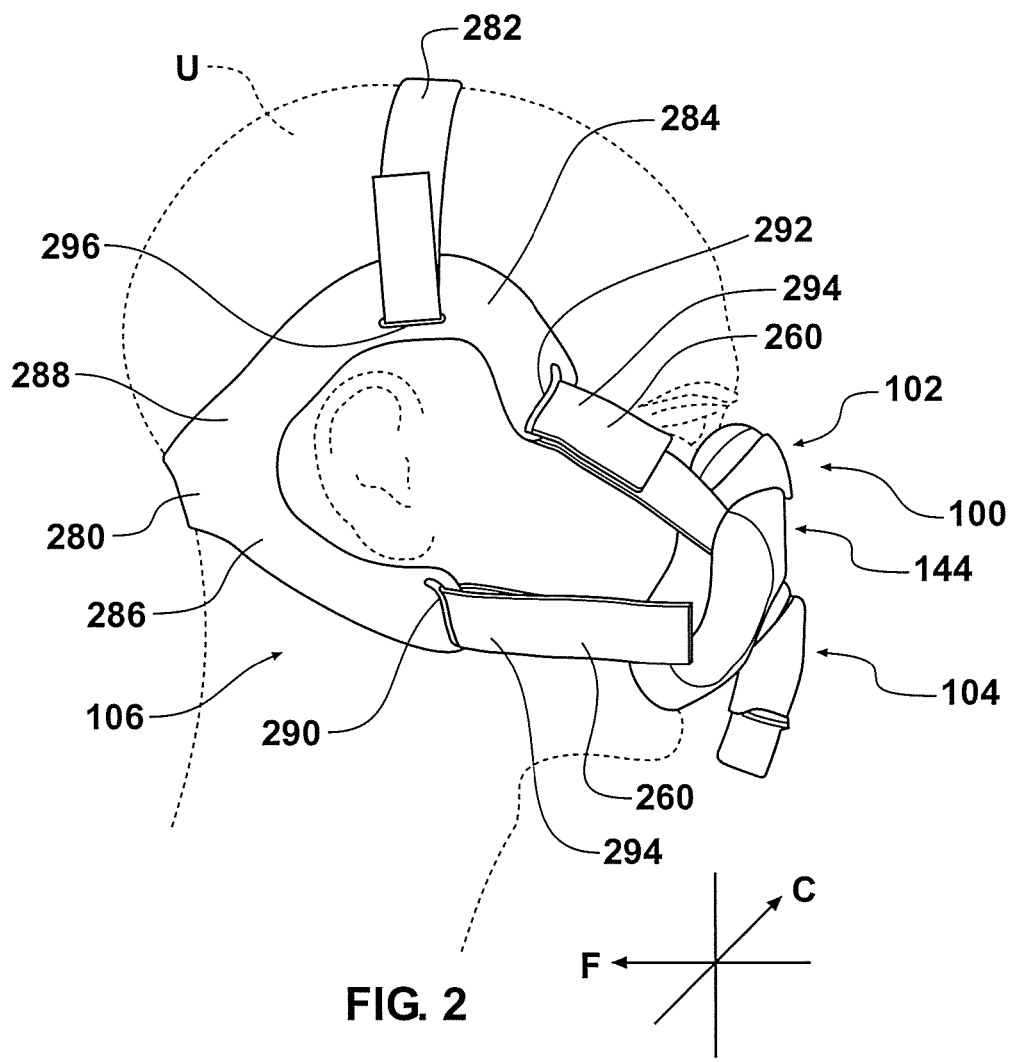
FIG. 2 is a side view of a user wearing the interface of FIG. 1.

With reference initially to FIGS. 1 and 2, an interface 100 is shown in position on a user U. The interface 100 comprises an interface that can be used in the field of respiratory therapy. The interface 100 has particular utility with forms of positive pressure respiratory therapy. For example, the interface 100 can be used for administering continuous positive airway pressure ("CPAP") treatments. In addition, the interface 100 can be used with variable positive airway pressure ("VPAP") treatments and bi-level positive airway pressure ("B iPAP") treatments. The interface can be used with any suitable CPAP system.

The interface 100 can comprise any suitable mask configuration. For example, certain features, aspects and advantages of the present disclosure can find utility with nasal masks, full face masks, oronasal masks or any other positive pressure mask. The illustrated mask is a full face mask. The illustrated interface 100 generally comprises a mask assembly 102, a connection port assembly 104 and a headgear assembly 106.

Figure 3:
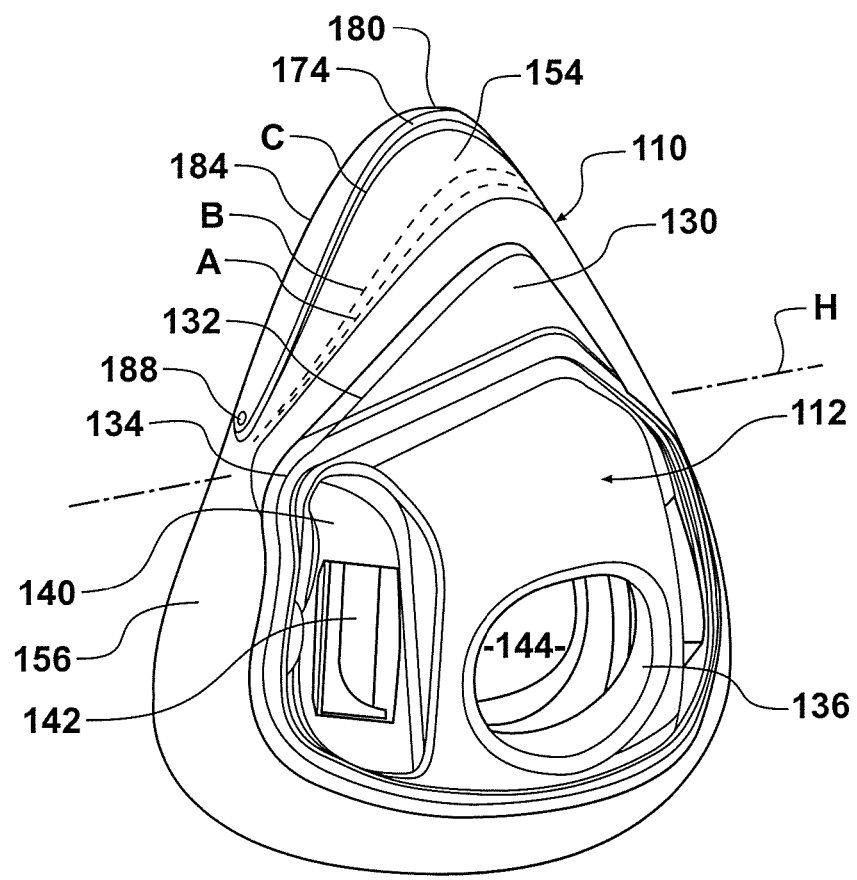
FIG. 3 is a perspective view of a mask seal and mask seal clip of the interface of FIG. 1.
Figure 4:
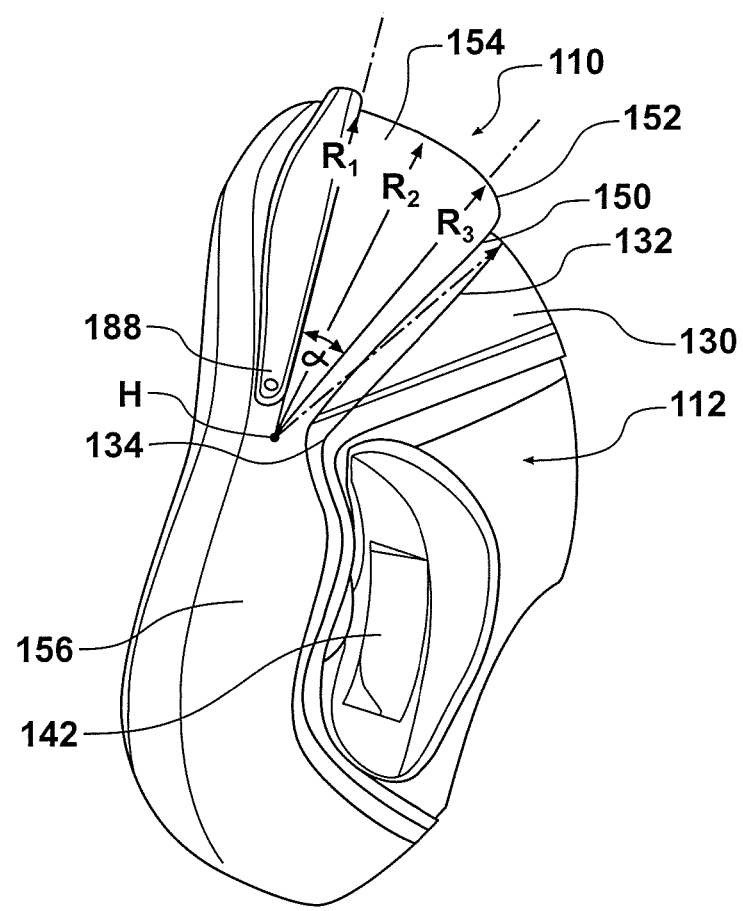
FIG. 4 is a side view of the mask seal and mask seal clip of FIG. 3.

With reference to FIGS. 3 and 4, the mask assembly 102 generally comprises a mask seal 110, which can include a mask seal clip 112, and a mask base 114. The mask seal clip 112 preferably connects the mask seal 110 to the mask base 114. While the illustrated mask seal 110 and mask seal clip 112 are formed separately and secured together, in some configurations, the mask seal 110 and the mask seal clip 112 can be integrated into a single component. In some configurations, the mask seal 110 is overmolded onto the mask seal clip 112.

With reference to FIG. 3, the mask seal clip 112 is relatively more rigid, stiffer or more inflexible than the mask seal 110. In some configurations, the mask seal clip 112 is formed of a polycarbonate material. In some configurations, at least a portion of the mask seal clip 112 is formed of a polycarbonate or other rigid or semi-rigid material. In some configurations, the mask seal clip 112 is formed at least partially of silicone or another suitable material. In such configurations, at least the silicone portion of the mask seal clip 112 may be formed to be relatively thicker compared to the more flexible portions of the mask seal 110. The mask seal clip 112 provides structural support to the mask seal 110 in the illustrated configuration.

The illustrated mask seal also comprises a generally central passage 144 that is defined by a wall 146. In the illustrated configuration, the wall 146 generally encloses the passage 144. Preferably, the wall 146 is generally cylindrical in configuration and extends through the wall 126. Other configurations are possible.

With reference to FIG. 4, the mask seal clip 112 preferably is arranged such that it is generally flush with an inner rim 150 of the mask seal 110. In the illustrated configuration, the mask seal 110 comprises a relatively small radius portion 152 that joins an upper portion 154. The upper portion 154 of the mask seal 110 is configured to extend over a nasal region of the user. In some configurations, the upper portion 154 is configured to extend over a nasal bridge region of the user U.

Figure 10:
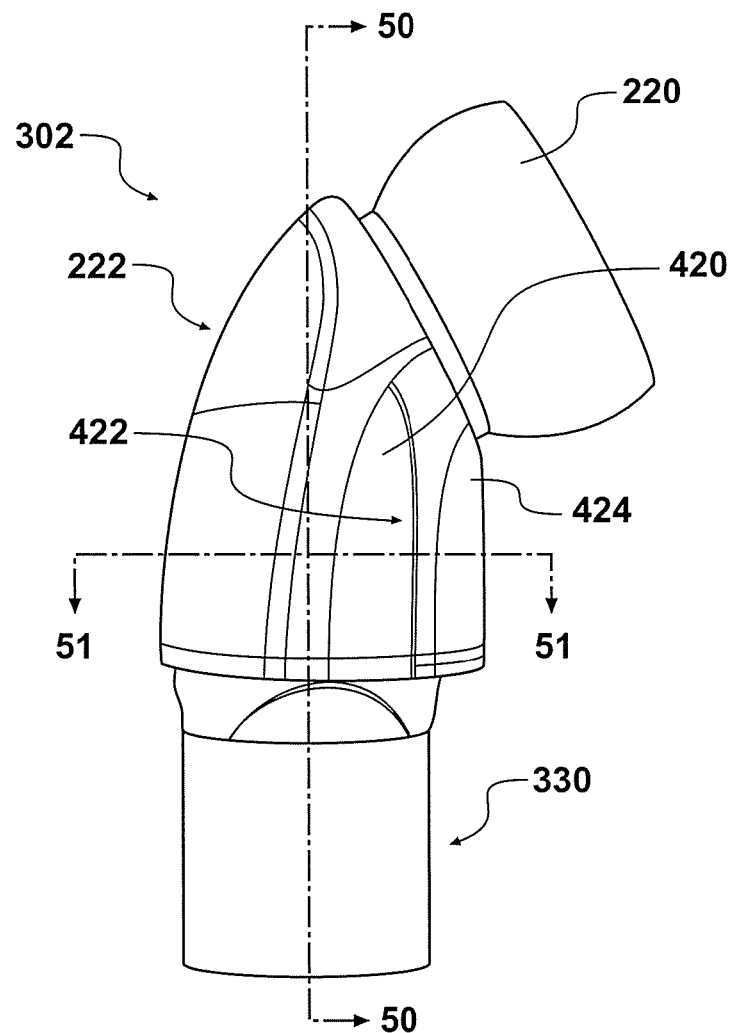
FIG. 10 is a side view of another configuration of a conduit connector assembly in the form of elbow assembly.

The upper portion 154 is connected with a lower portion 156 of the mask seal 110. The lower portion 156 extends laterally outward from the mask seal clip 112. In addition, the lower portion 156 wraps rearward and inward, as shown in FIG. 4. Together, on a proximal side of the full face mask assembly 102, the upper portion 154 and the lower portion 156 combine to define a face contacting flange 160, which is shown in FIG. 10. The face contacting flange 160 is configured to underlie a lower lip of the user, extend along the outside of the mouth, extend upward along the cheekbones and extend across the bridge of the nose of the user. Thus, the illustrated face contacting flange 160 defines a generally tear-drop shaped opening 162. When the mask assembly 102 is seated on the face of the user, the flange 160 will lie flat over the bridge of the nose, the cheekbones, the outside of the mouth and below the lower lip of the user. With a supply of positive pressure air, the mask seal 110 will balloon and seal against the face of the user to reduce or eliminate the likelihood of leakage between the flange 160 and the face of the user.

The upper portion 154 of the mask seal 110 is designed to roll over onto an outer surface 170 of the mask assembly 102. In the illustrated configuration, the outer surface of the mask seal 110 smoothly rolls into abutment with the outer surface of the mask seal clip 112 such that the outer surface of the mask seal clip 112 forms a support surface. In some configurations, the outer surface 170 onto which the upper portion 154 rolls comprises at least a portion of the outer surface of the mask seal clip 112. In some configurations, the outer surface 170 onto which the upper portion 154 rolls comprises almost exclusively the outer surface of the mask seal clip 112. In some configurations, the upper portion 154 rolls onto another portion of the mask seal 110. In some configurations, the upper portion 154 rolls onto the mask base 114.

With reference now to FIGS. 1 and 2, the mask assembly 102 includes the mask base 114, which is more rigid than the mask seal 110. The mask base 114 can be formed of any suitable material. In some configurations, the mask base 114 is formed of a polycarbonate material such that it is capable of flexing for connection with the mask seal 110 and/or the mask seal clip 112.

Figure 5:
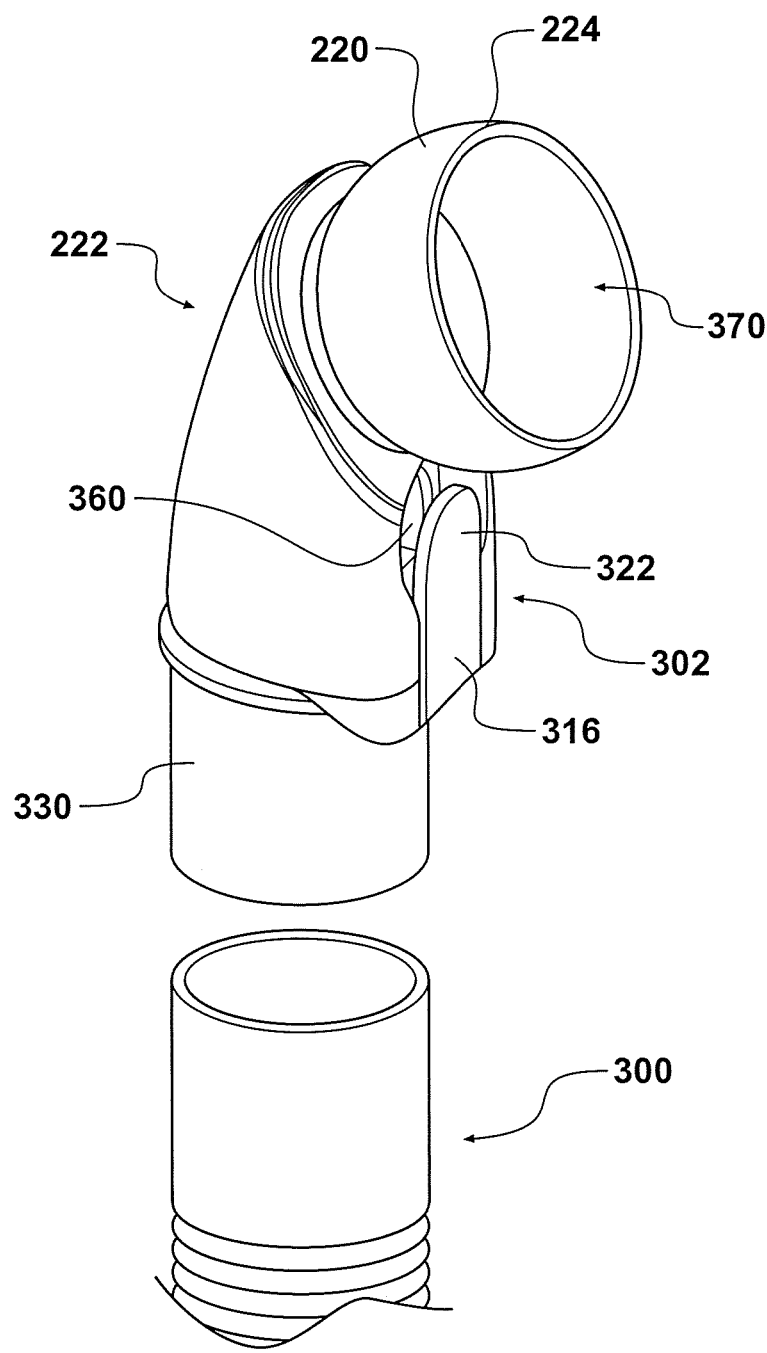
FIG. 5 is a perspective view of a conduit connector assembly in the form of an elbow assembly arranged to be connected to the interface of FIG. 1.
Figure 6:
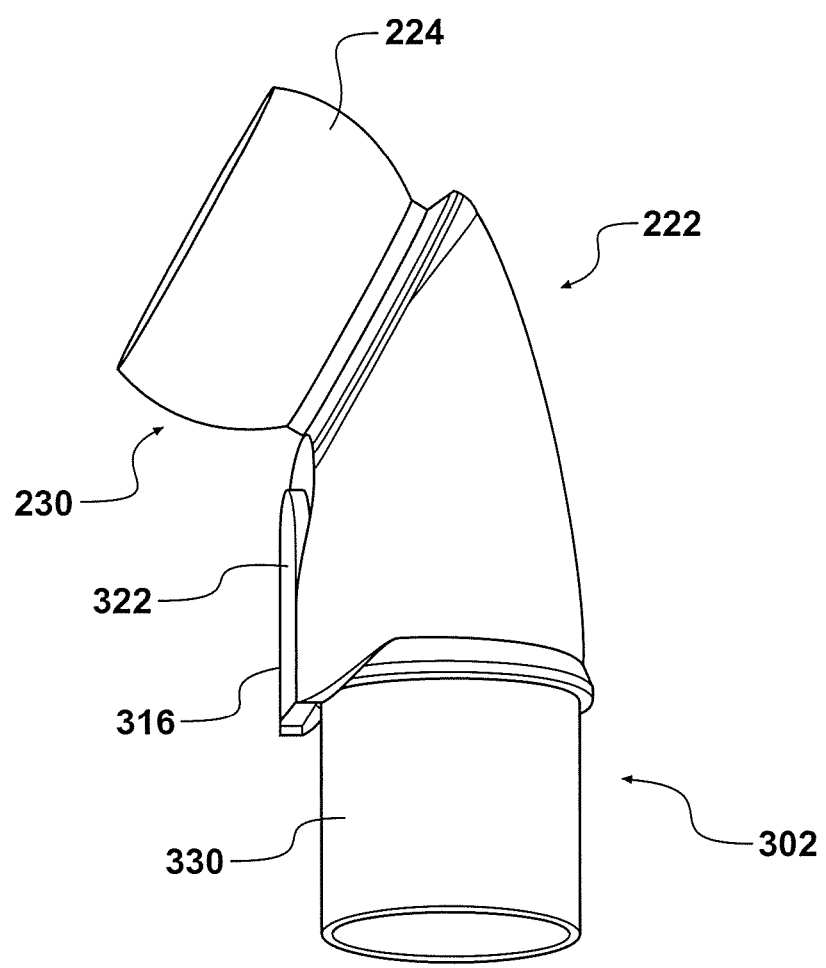
FIG. 6 is a side elevation view of the elbow assembly of FIG. 5.
Figure 7:
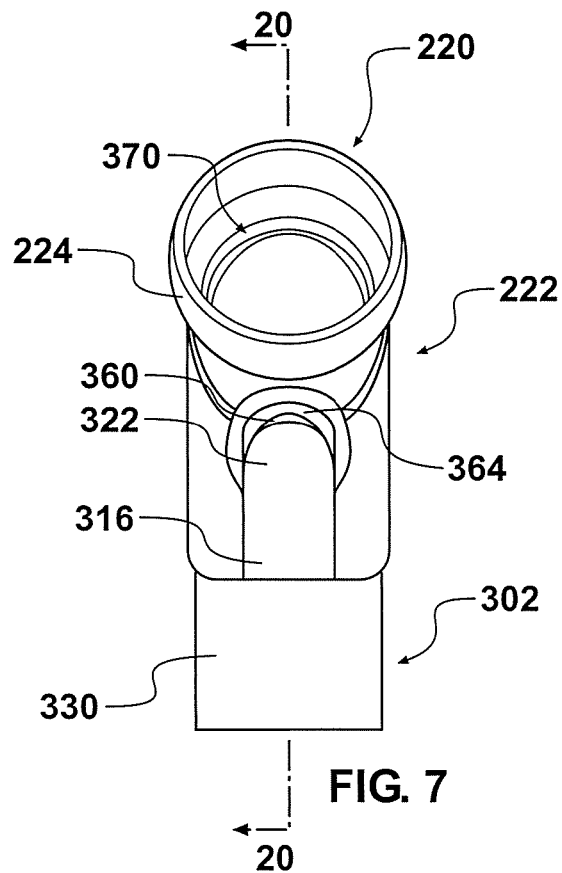
FIG. 7 is a rear elevation view of the elbow assembly of FIG. 5.

Central passage 144 may be configured to connect to a conduit connector assembly. For example, central passage 144 may be radiused to receive a ball end 220 of a conduit comprising a swiveling elbow 222, such as that shown in FIG. 5. As better shown in FIG. 6, the ball end 220 has a contoured surface 224 that can be snap fit into the contoured surface 214 formed in the mask base 114. The connection between the two contoured surfaces 214, 224 allows the surfaces to slide relatively freely with each other such that the position of the swiveling elbow 222 can be easily changed. In some configurations, the elbow 222 could be configured for rotation or swiveling without having a ball-joint configuration.

With reference to FIG. 2, in addition to the straps 260, the headgear assembly 106 also comprises a back strap 280 and a top strap 282. Other head gear assemblies also can be used. The back strap 280 extends around the back of the head of the user U at a location generally above a nape of the neck but generally below the occipital protuberance. At a location rearward of the ear of the user, the back strap 280 forks into an upper arm 284 and a lower arm 286. The upper arm 284 arcs upward to a location above the ear of the user and then arcs downward to a location generally forward of the ear of the user. The lower arm 286 arcs downward to a location generally below the ear of the user and extends slightly forward of the ear.

The straps 260 can be connected to the back strap 280 in any suitable manner. In the illustrated configuration, the straps 260 connect to the upper arm 284 and the lower arm 286 respectively. Preferably, the upper arm 284 and the lower arm 286 are more rigid than the straps 260 such that the arms 284, 286 generally maintain shape as the headgear assembly 106 is being donned. In some configurations, each of the upper arm 284 and the lower arm 286 supports its own weight. In some configurations, each of the upper arm 284 and the lower arm 286 is structured to be tangle-free during donning. For example, the arms 284, 286 have sufficient torsion stiffness to reduce the likelihood of twisting when being put on.

Preferably, the straps 260 connect to at least one of the upper arm 284 and the lower arm 286 at a location forward of the ear. Such a configuration helps the user to locate the straps 260 without much difficulty. In addition, because the straps 260 in the illustrated configuration are embedded into the clips 252, the ends of the upper arms 284 and the lower arms 286 can comprise slots 290, 292 such that the straps 260 can be threaded through the slots 290, 292. In addition, the straps 260 can comprise an adjustment mechanism 294, such as a Velcro or buckle configuration. The adjustment mechanism 294 allows a force between the mask seal 110 and the face of the user U to be adjusted. Any suitable adjustment mechanism 294 can be used.

As shown in FIG. 2, the top strap 282 preferably is flexible and has an adjustable length. The top strap 282 connects to the upper arms 284 through a slot 296 and reduces the likelihood of the upper arms 284 sliding down the head of the user and contacting the ears of the user. Preferably, the top strap 282 connects to the upper arms 284 at a location generally above the ears of the user.

Advantageously, as shown in FIGS. 1 and 2, the straps 260 exert a force in the direction of the arrow F while they connect to the mask base 114 by movement in the direction C, which direction is generally normal to the direction of the force F. In other words, the straps 260 are tensioned by pulling forward and the clips 252 are connected to the mask base 114 by movement in a direction normal to the forward pull. Such a configuration eases securement of the interface 100 on the face of the user.

With reference again to FIG. 5, the elbow 222 connects to a conduit 300 through a disconnectable swivel assembly 302. As shown in the section view of FIG. 8, the elbow 222 comprises a stem 304 that comprises an inner wall 306 at the base. The inner wall 306 comprises a recess 308.

Figure 9:
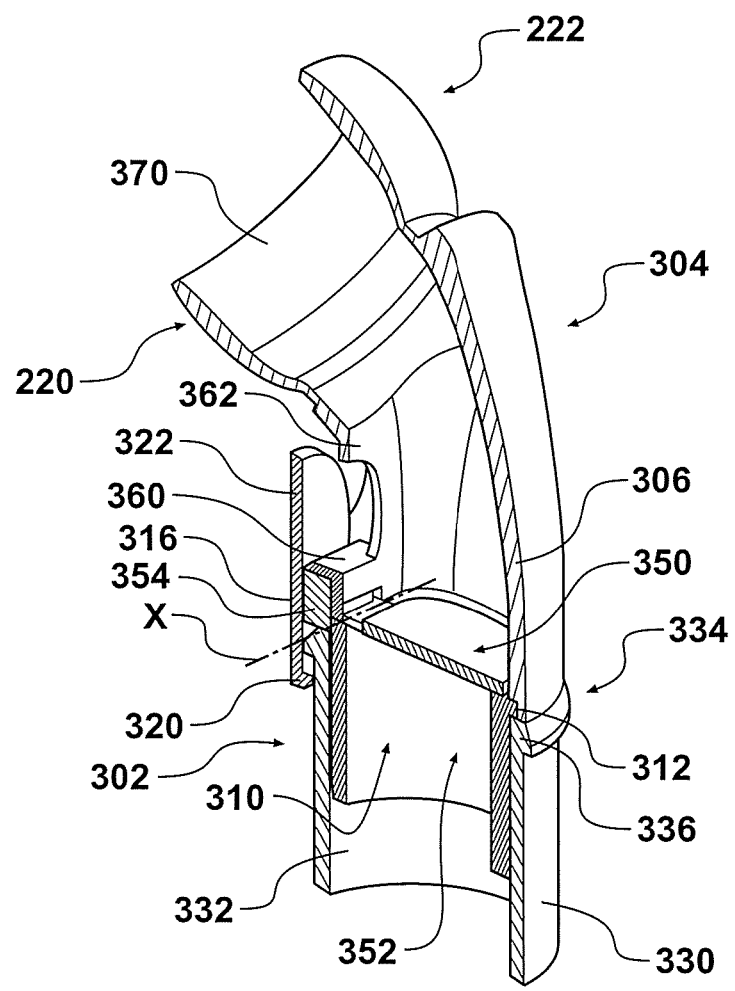
FIG. 9 is a sectioned perspective view of the elbow assembly of FIG. 5.

A sleeve 310 comprises a flange 312 that is received within the recess 308. The sleeve 310 can be secured into position within the elbow 222 using any suitable technique. The sleeve 310 comprises a generally cylindrical outer wall 314. The flange 312 comprises a section that extends outward to connect to a lever 316. Preferably, the flange 312 and the lever 316 are integrally formed. With reference to FIG. 9, the lever 316 includes a lower inwardly extending catch 320 and is capable of pivoting about the section that connects the lever 316 to the flange 312. Thus, pressing inward on an upper portion 322 of the lever 316 results in the catch 320 moving away from the generally cylindrical outer wall 314 of the sleeve 310.

A swivel 330 comprises a generally cylindrical inner wall 332. The inner wall 332 slides over the outer wall 314 of the sleeve 310 such that a sliding fit results between the swivel 330 and the sleeve 310. An upper portion 334 comprises a shoulder 336. The catch 320 of the lever 316 can secure the swivel 330 in axial position on the sleeve 310 by engaging with the shoulder 336. When the upper portion 322 of the lever 316 is depressed, the catch 320 moves away from the shoulder 336, which allows the swivel 330 to be removed from the sleeve 310.

Figure 8:
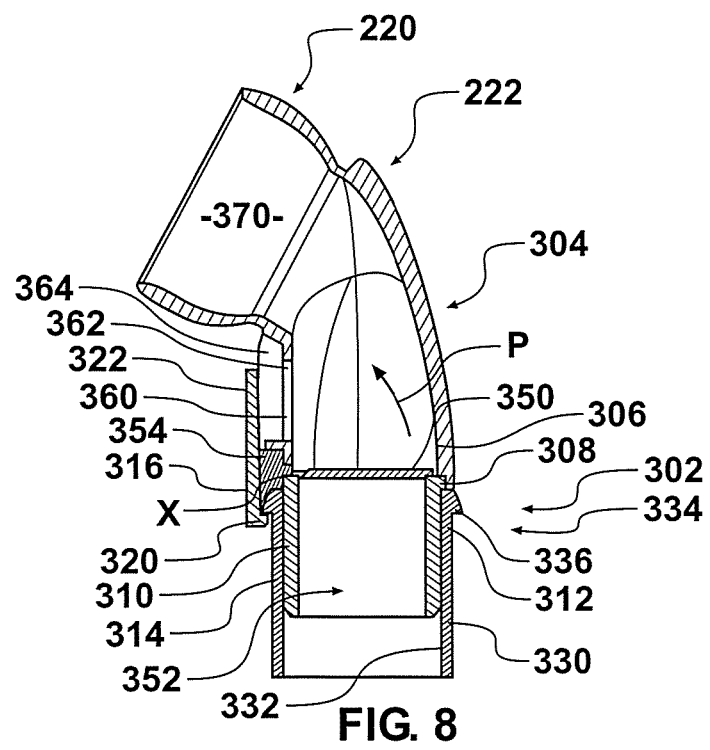
FIG. 8 is a sectioned side elevation view of the elbow assembly of FIG. 5.

A flap 350 can be mounted between the stem 304 and the sleeve 310. In the illustrated configuration, the flap 350 extends into a flow channel 352 from a base 354 that is sandwiched between the stem 304 and the sleeve 310. The flap 350 can pivot upward (as shown in FIG. 8, see arrow P) about an axis X (see FIG. 9) away from the sleeve 310 such that flow from a positive pressure generator can continue generally unobstructed to the user through the interface 100. The flap 350 pivots downward into contact with the sleeve 310 to seal the flow channel 352 in the event that the positive pressure source stops providing a pressurized flow of air. In some configurations, the flap 350 will not fully contact the sleeve 310. In some configurations, the flap 350 will not seal the channel 352 when in the down position.

With reference to FIG. 9, a port 360 is defined through the elbow 222 at a location above the flap 350. The port 360 preferably is positioned along a portion of the elbow 222 that is in the vicinity of the axis X. In some configurations, the port 360 is positioned to be substantially shielded by the flap 350 from an inspiratory flow of air. In other words, as the air pivots the flap 350 away from the sleeve 310, the flap 350 is moved into a position that at least partially or completely covers the port 360.

In some configurations, the port 360 extends through a wall of the elbow 222 that comprises a generally planar inner wall 362. The generally planar inner wall 362 helps the flap 350 to generally seal the port 360 when the flap is moved upward away from the flange 312 of the sleeve 310.

In some configurations, the lever 316 overlies a majority of the port 360 such that the port 360 is generally obscured from view. As shown in FIG. 8, however, a gap 364 preferably surrounds at least a portion of the lever 316 such that a relatively free flow of air can pass through the port 360 when the flap 350 does not overly the port 360. In addition, in some configurations, the port 360 and the lever 316 are positioned on a same side of the elbow 222 as an opening 370 defined within the ball end 220, which opening is positioned within the mask assembly 102 when the connection port assembly 104 is assembled to the mask assembly 102. Advantageously, such a positioning places the port 360 in a position on the elbow 222 that faces the user. Such a location further obscures the port 360 from view during use, which results in a more aesthetically pleasing configuration. Moreover, because flow through the port 360 will be very infrequent, having the port 360 disposed toward the user will not cause any significant discomfort for the user.

While not shown, the elbow 222 also can comprise one or more bias flow vent holes. The bias flow vent holes preferably are positioned in a forwardly directed orientation such that any bias flow does not directly impinge upon the user.

Figure 11:
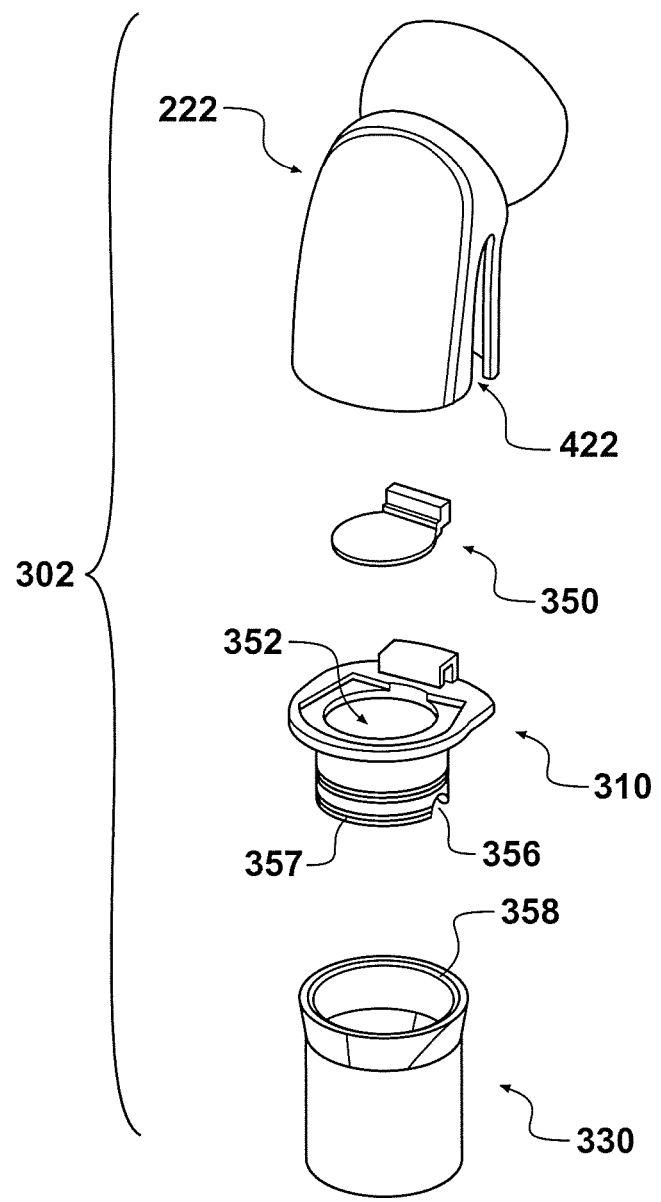
FIG. 11 is an exploded view of the elbow assembly of FIG. 10.
Figure 12:
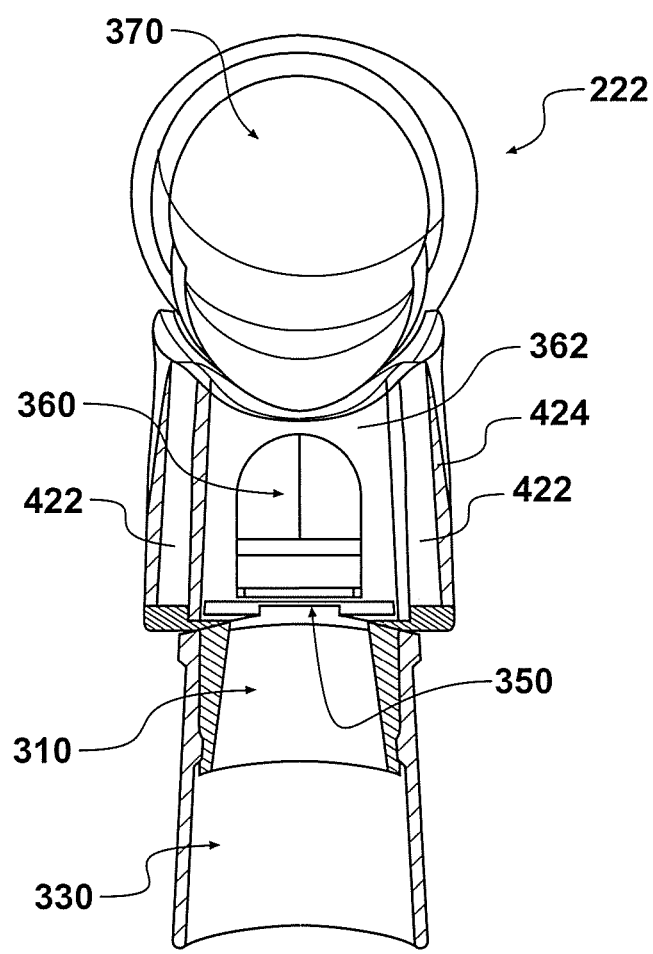
FIG. 12 is a cross-sectional view taken along line 50-50 of FIG. 10.
Figure 13:
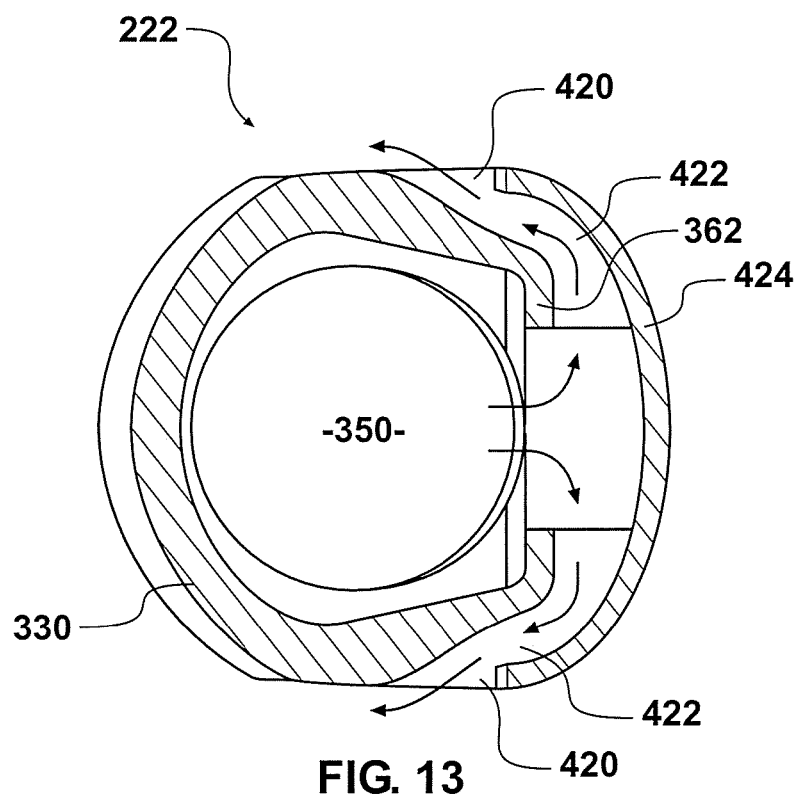
FIG. 13 is a cross-sectional view taken along line 51-51 of FIG. 10.

Another configuration of an elbow assembly 302 is illustrated in FIGS. 10-13. The elbow assembly 302 comprises an elbow 222, a sleeve, 310, and/or a swivel 330, as shown in FIG. 11. In some configurations, the elbow assembly 302 only includes the elbow 222 and sleeve and omits the swivel 330. The swivel may be permanently or removeably attached to the sleeve 310 and elbow 222; in some configuration, the swivel 330 is integrally formed with the end of the delivery conduit. An anti-asphyxia valve flap 350 is positioned over the sleeve 310 such that it at least partially obstructs the sleeve's flow channel 352. The elbow assembly 302 functions similarly to the elbow assembly 302 of FIGS. 5-9; however, the elbow assembly 302 of FIGS. 10-13 provides the additional benefit of directing gases away from the patient when the flap 350 drops to its closed position (as shown in FIGS. 12 and 13).

With reference to FIG. 11, the sleeve 310 preferably comprises two or more cut out regions or recesses 356. The recesses 356 can have any suitable shape and, in the illustrated configuration, the recesses 356 comprise a semicircular configuration that extends upward into the sleeve 310. The sleeve 310 also comprises at least one bump 357, and preferably two or more bumps 357. Preferably, each of the bumps 357 extends around an arc of about 70 degrees. More preferably, each of the bumps 357 is generally centered between two recesses 356 and each of the bumps 357 extends about 70 degrees around an outer surface of the sleeve 310.

The swivel 330 preferably is generally cylindrical in configuration. As shown in FIG. 11, the swivel 330 has an inwardly extending ridge 358. The ridge 358 preferably encircles the entire inner surface. In some configurations, the ridge 358 can be interrupted. Preferably, however, the ridge 358 does not have any interruptions large enough to accommodate the entire bump 357 such that the ridge 358 and the bump 357 can cooperate to keep the swivel 330 mounted over the sleeve 310. When assembling the swivel 330 to the sleeve 310, the recesses 216 allow the bumps 357 to deflect inward such that the bumps 357 can slide over the ridge 358 and then snap back outward to secure the bumps 357 under the ridge 358.

The elbow 222 comprises expiratory flow ports 420 at its sides that are in fluid communication with an air venting channel 422. The air venting channel 422 is formed by the spacing between the elbow's inner and outer walls 362, 424, as shown in FIGS. 12 and 13.

When the flap 350 drops to its closed position, as shown in FIGS. 12 and 13, air exhaled from the user enters opening 370 of the elbow 222. The exhalation flows through the port 360 in the elbow's inner wall 362, and through the venting channel 422 until it exits the elbow 222 via the expiratory flow port 420.

The configuration of FIGS. 10-13 provides a reduced overall length and improves product aesthetic by eliminating an unsightly hole positioned at the front of the elbow 222. In addition, the configuration of FIGS. 10-13 and improves patient comfort by preventing air from being directed towards the user. Instead, expiratory flow ports 420 direct air flow out of the sides of the elbow 222 and away from the patient.

Referring additionally to FIGS. 14 to 19, another configuration of an elbow assembly 702 comprises an elbow 722 and a sleeve 710. The swivel 330 as described above may also be provided but is not illustrated in FIGS. 14 to 19.

Figure 14:
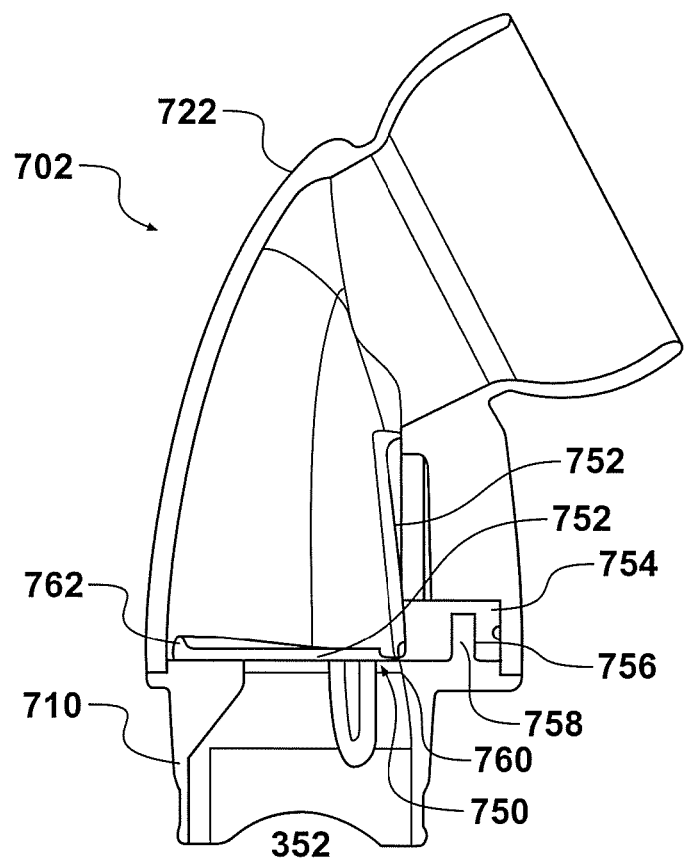
FIG. 14 is an enlarged cross-sectional side view of another conduit connector assembly in the form of an elbow assembly, with an anti-asphyxia valve flap in an open and a closed condition.
Figure 15:
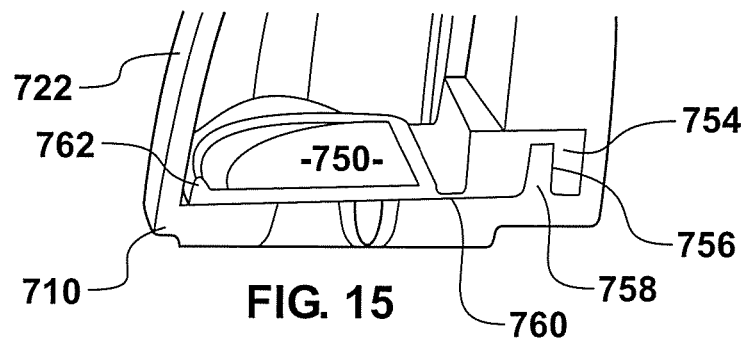
FIG. 15 is an enlarged cross-sectional side and perspective view of part of the elbow assembly of FIG. 14.
Figure 16:
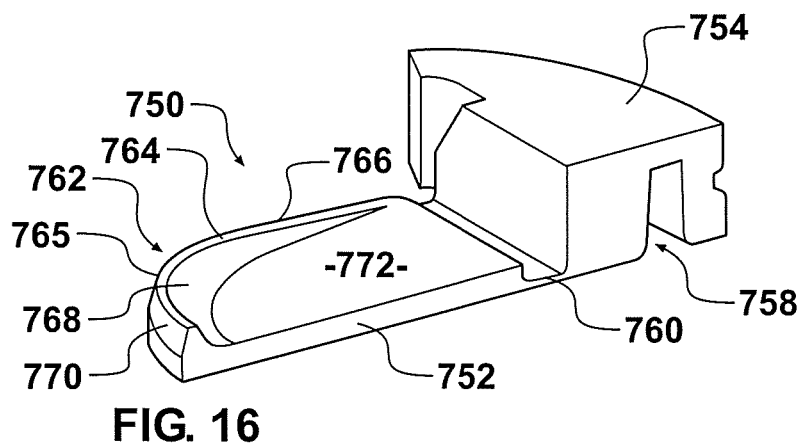
FIG. 16 is an enlarged perspective view of part of an anti-asphyxia valve of the elbow assembly of FIG. 14.
Figure 17:
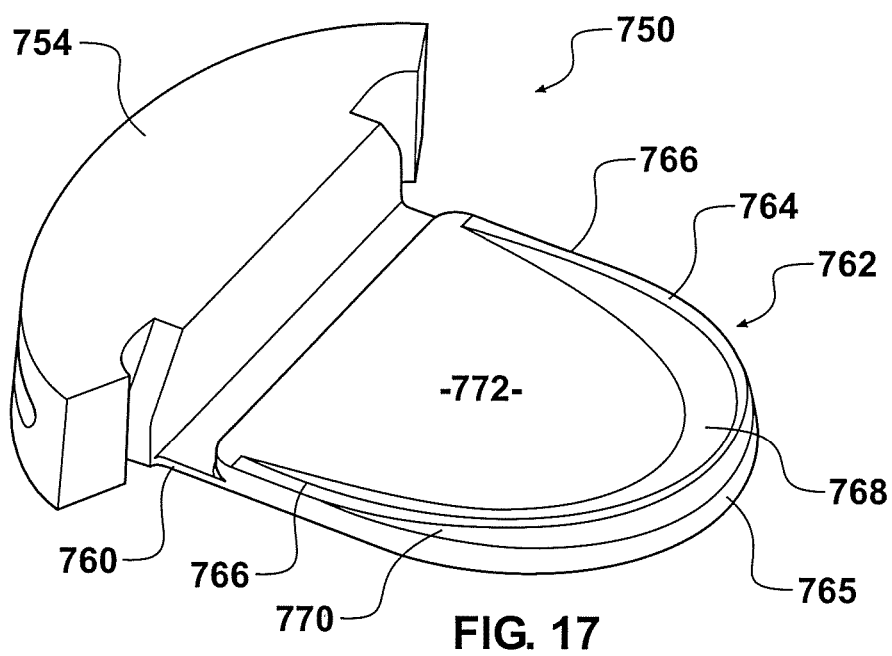
FIG. 17 is another enlarged perspective view of part of the anti-asphyxia valve of the elbow assembly of FIG. 14.
Figure 18:
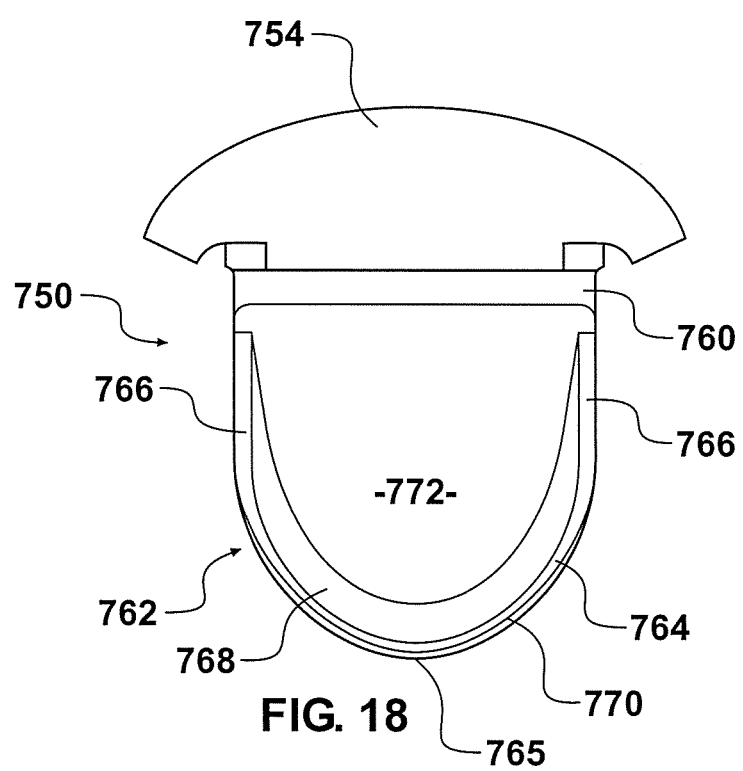
FIG. 18 is a plan view of part of the anti-asphyxia valve of the elbow assembly of FIG. 14.

An anti-asphyxia valve (AA valve) 750 is provided and positioned over the sleeve 710 such that it at least partially obstructs the sleeve's flow channel 352. The elbow assembly 702 functions similar to the elbow assembly 302 of FIGS. 10 to 13, and similarly directs gases away from the patient when the flap 752 of the AA valve 750 drops to its closed position, namely the generally horizontal position as shown in FIG. 14, closing the flow channel 352 through the sleeve 710.

The AA valve 750 comprises generally planar valve flap 752 which is hingedly mounted on a flap support 754. The flap support 754 may be integrally formed with the valve flap 752, and may comprise one or more orientation features which facilitate correct orientation and mounting of the valve 750 on the sleeve 710. In this example an orientation feature comprises a slot 756 formed in the underside of the flap support 754 which receives a corresponding protrusion 758 provided on an upper part of the sleeve 710. The engagement between the slot 756 and protrusion 758 helps retain the valve 750 on the sleeve 710 during assembly of the elbow assembly 702, and assists in correctly orientating the valve 750 relative to the sleeve 710 and elbow 722, and relative to the axis of the sleeve's flow channel 352. The slot 756 and protrusion 758 also prevent the valve 750 from being mounted on the sleeve 710 upside down, that is, with the flap 752 and flap support 754 rotated 180 degrees from the orientation illustrated in FIG. 14.

The AA valve 750 comprises a hinge 760, pivotally mounting the flap 752 on the support 754. The hinge 760 may be integrally formed with both the flap 752 and the support 754. The hinge 760 comprises a relatively thin strip of material which is of greater flexibility than the flap 752 and the support 754, enabling the thicker flap 752 to pivot about the support 754 from a generally horizontal position in which the flap 752 closes the flow channel 352 through the sleeve 710, to a generally vertical position in which the flap 752 opens the flow channel 352 in the sleeve 710 but closes the air venting channels 422 formed in the elbow 722.

The valve flap 752 comprises a bead 762 or ridge or protrusion which protrudes from a planar upper surface 764 of the flap 752. The bead 762 thus projects from the upper surface 764 of the flap 752. When the flap 752 is in the generally vertical position in which the flap 752 opens the flow channel 352 in the sleeve 710 but closes the air venting channels 422 formed in the elbow 722, the bead 762 contacts the part of the elbow 722 surrounding the venting channels 422, and forms a discrete sealing upper surface 764 which seals against the elbow 722 and closes the venting channels 422. The bead 762 thus forms a sealing upper surface 764 having a relatively small sealing area relative to the area of the valve flap 752 itself. That is, the area of the bead 762 which seals against the elbow 722 when the flap 752 is in the generally vertical condition is relatively small, but still sufficient to seal the venting channels 422 closed.

When the elbow 722 has gone through multiple cleaning cycles, the plastic surfaces of the elbow 722 can become degraded, allowing water to more easily stick to those surfaces. Thus, the wetting angle of the water/plastic interface increases with the result that water droplets can sit on the contact surfaces of the elbow 722, rather than forming beads and rolling off the contact surfaces.

It can be a problem with prior art AA valves that the relatively large sealing surface of a planar valve flap can trap water between the contact surfaces of the elbow and the valve flap. The surface tension of the water can cause the water to act as an adhesive, sticking the valve flap against the elbow contact surfaces, such that the valve flap sticks in the generally vertical condition, closing the venting channels 422.

Providing bead 762 on the valve flap 752 creates a much smaller relative sealing surface in contact with the internal sealing surfaces of the elbow. This results in the amount of water between the flap and the elbow being lower, lowering the force that the water's surface tension can resist, and allowing the valve flap 752 to release from the elbow contact surfaces more easily. The provision of the bead 762 thus reduces or prevents the valve flap 752 sticking in the position where the venting channels 422 are closed.

In this example the bead 762 comprises an arcuate, curvilinear portion 765 which follows the curved periphery of the valve flap 752 distal from the hinge 760, and linear portions 766 which extend along the straight sides of the valve flap 752, towards the hinge 760. The bead 762 in this example therefore extends substantially around the entire periphery of the valve flap, to the hinge 760 and is substantially 'n' shaped when viewed in plan.

In this example, the bead 762 is tapered when viewed from the side. Thus, part of the bead 762 distal from the hinge 760 protrudes further from the planar upper surface 764 of the flap 752 than the parts of the bead 762 nearer the hinge 760. In this example, the apex of the arcuate, curvilinear portion 765 projects further from the flap 752 than the linear bead portions 766. The bead tapers uniformly from the arcuate, curvilinear portion 765 to the linear portions 766, such that the bead 762 blends into the upper planar flap surface adjacent the hinge 760. This tapering along the longitudinal axis of the valve flap 752 allows the bead 762 to fully seal against the sealing surfaces of the elbow 722 around the entire periphery of the flap 752, to close the venting channels 422. The flap 752, when in the upright condition which closes the venting channels 422, is thus slightly inclined from the vertical when sealing against the elbow 722.

In this example, the profile of the bead 762 when viewed from the side, is rounded or chamfered. Thus, the sealing upper surface 764 of the bead 762, that is, the part of the bead 762 which protrudes the most from the valve flap 752 may be flat. However, the side walls of the bead which support the bead sealing upper surface 764 may be profiled, and may be rounded or chamfered for example. The profiled side walls 768, 770 of the bead 762 may extend all of the distance to the valve flap 752, or may be profiled only adjacent the sealing upper surface 764. As can be seen from FIG. 17 for example, the profile of one side wall 770 of the bead 762 may be different from the profile of the other side wall 772 of the bead 762. In this example, the inside side wall 768 of the bead 762 curves down from the sealing upper surface 764 and blends into the upper planar surface 764 of the valve flap 752 over a relatively large radius of curvature, that is, a relatively shallow curve from the bead sealing upper surface 764 to the valve flap 752. In contrast, the outside side wall 770 of the bead 762 is straight and has a relatively steep, straight angle of inclination from the bead sealing upper surface 764 to the valve flap 752.

Other profiles and shapes of bead are envisaged. For example, the bead may simply comprise a square, rectangular, oblong or triangular cross sectional profile. For example the cross section of the bead may vary along the length of the bead. Part or all of the bead 762 may comprise a semi-circular or arcuate cross sectional profile. The side walls of the bead 762 may not be rounded or chamfered, and may simply be straight sides extending between the bead sealing surface 764 and the valve flap 752. The straight sides may be inclined, or substantially perpendicular relative to the plane of the valve flap 752.

Figure 19:
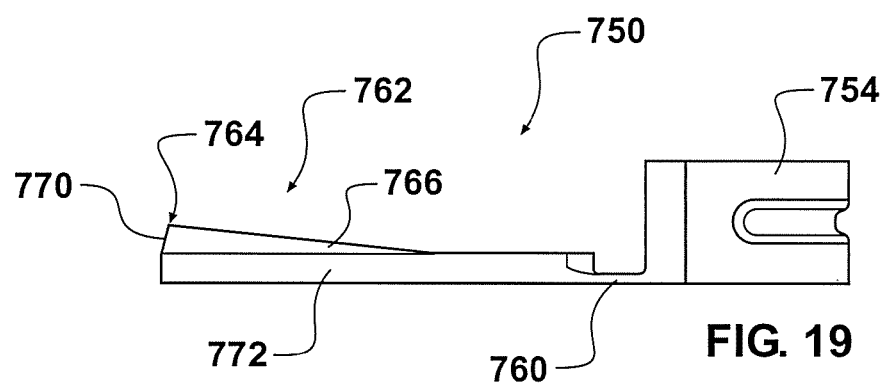
FIG. 19 is side view of part of the anti-asphyxia valve of the elbow assembly of FIG. 14.
Figure 20:
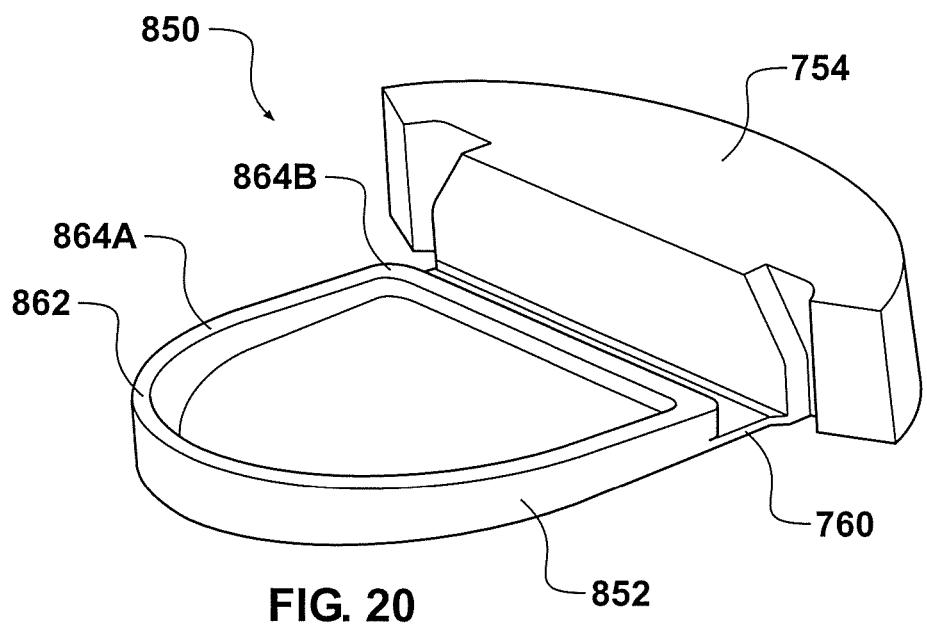
FIG. 20 is a perspective view of another embodiment of an anti-asphyxia valve.
Figure 21:
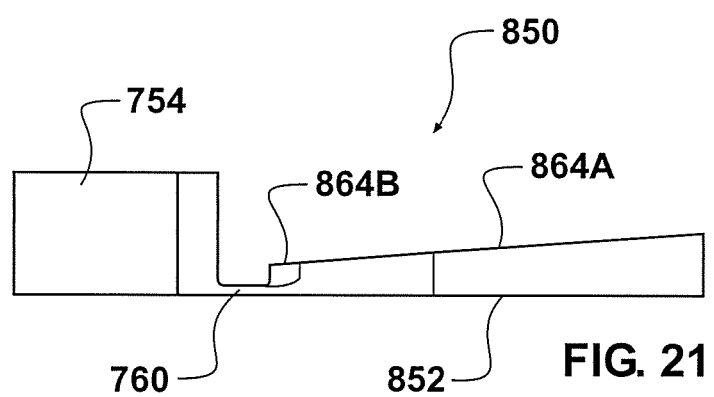
FIG. 21 is a side view of the valve of FIG. 20.

Referring to FIGS. 19 and 20, another embodiment of an anti-asphyxia valve 850 comprises many similar features to the valve 750 described above. However, in this example, the valve 850 comprises a bead 862 which extends around the entire periphery of the valve flap 752, with part of the bead 862 extending past the hinge 760. The bead 862 in this example is therefore substantially 'D' shaped when viewed in plan and comprises a sealing surface 864A extending away from the hinge 760, and a sealing surface 864B extending adjacent to and parallel with the hinge 760.

In this example, an alternative bead profile is provided. In this example, the side walls of the bead are substantially straight, and are not inclined with respect to the plane of the valve flap 852. Likewise, the sealing surface 864A in this example is straight when the bead 862 is viewed from the side, that is the sealing surface 864 is a planar surface with the plane inclining downwardly from the distal part of the flap 852 towards the hinge 760. Thus the bead 862 is tapered as with the bead 762, but the sealing surface 864A is straight with no curved or inclined regions when viewed from the side. This may enhance the seal provided between the sealing surface 864A and the elbow, and may reduce the likelihood of leak paths forming. The bead 862 in this example is also more rigid, which may help prevent the flap edges from lifting and leaking at lower pressures, due to the flap 852 bending.

Figure 22:
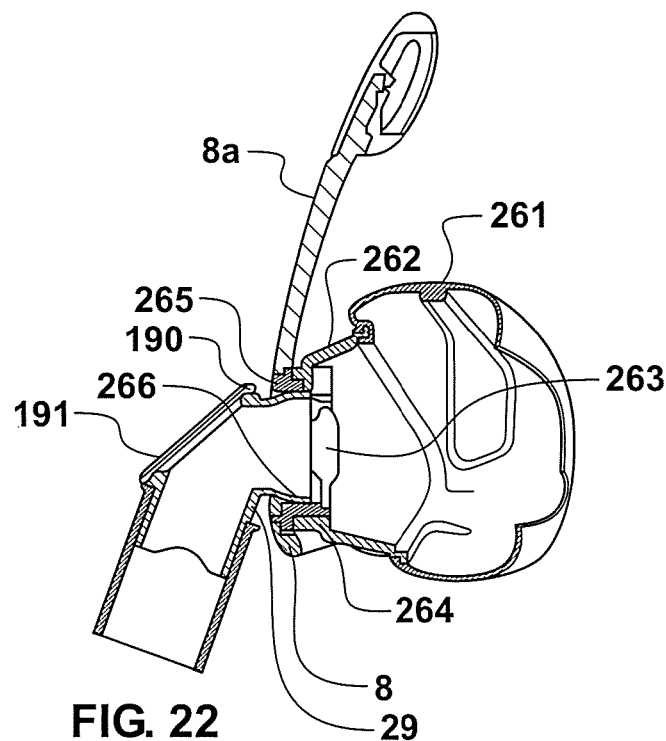
FIG. 22 is a cross-sectional view of a patient interface assembly.

FIG. 22 is a sectional view of a patient interface including a soft seal 261 which is fixed to a rigid or more rigid shell 262. The shell 262 comprises a gases entry opening 263 with therearound an outwardly (or alternatively inwardly) projecting annular shell collar 264. Annular mounting collar 265 is mounted into frame 8 in a suitably shaped aperture in frame 8, which a click fit or snap fit, or is welded in place, and mounting collar 265 receives annular shell collar 264 preferably with a click fit or snap fit. The upper annular end 266 of the elbow 29 fixes into the internal diameter of mounting collar 265, for example in a click or snap fit, when the mask is assembled for use, so that the elbow is coupled to the annular mounting collar 265 (rather than to the frame or shell). Alternatively, the seal-shell component may comprise a single material seal component. Annular mounting collar 265 may be a different material and/or color to the material and/or color of frame 8. Further details of this patient interface are disclosed WO2015/057087, the entire contents of which are incorporated herein by reference.

The patient interface of FIG. 22 further comprises or is configured to connect to a connector 267, preferably via a snap fit, as shown. The outer surface 268 of connector 267 is configured to be received in a respiratory tube (not shown) or a collar connector provided at a patient end of a respiratory tube (also not shown). The connector 267 shown in FIG. 22 is configured to sealably engage the respiratory tube (or the collar terminating the respiratory tube) by a friction fit. To this end, one or more of the engaging walls may be tapered. For example, the outer surface 268 of connector 267 may have a narrower or smaller external dimension near first end 271, and a wider or larger external dimension at some point between said first end 271 and second end 272 of connector 267. Additionally or alternatively, the opening (internal dimension) of the respiratory tube may vary from a location near its mouth having a relatively large dimension to a smaller or narrower dimension at a location axially inward in the respiratory relative, the dimension and location of the narrower portion being relative to the wider portion. As will be appreciated, where the respiratory tube is provided with a collar termination, the tapering may be formed in said collar rather than the respiratory tube.

A problem with the arrangement in FIG. 22 is that it is possible for a user to push connector 267 onto elbow 29 in the reverse direction, for example with second end 272 proximate the patient interface and first end 271 distil therefrom. Due to the tapering of the wall(s) and the fact that the internal dimension of the connector is approximately the same as the outer dimension of the elbow 29, collar 265 may frictionally engage the elbow in this configuration. This is not ideal since the connection between the connector 267 and the elbow 29 may be compromised. Further, it can be difficult to remove the connector 267 from the elbow 29 or the respiratory tube (or terminating collar thereof) from the connector 267. More particularly, the provision or engagement of the respiratory tube with the connector 267 can exert pressure on the connector 267, tightening the fit between the connector 267 and the elbow 29. This can be exacerbated when the respiratory tube or collar therefor is pushed too far onto the connector 267 towards the patient interface.

To address these problems, a new connector 270 has been devised, as shown in FIGS. 23a-25f. FIGS. 23a-23d show the connector 270 coupled to an elbow similar to elbow 29 of FIG. 22. FIGS. 24a-24c show the elbow of FIGS. 23a-23d and FIGS. 25-25f show the connector of FIGS. 23a-23d.

Connector 270 has first end 271 and second end 272. First end 271 is configured to couple to an elbow (such as elbow 29 shown in FIG. 22) or to a projecting collar otherwise forming a gases pathway with the interior of a patient interface or mask. For example, in a simpler arrangement, an elbow may be omitted and the connector may couple with a collar extending from the patient interface, that collar being integrally formed or coupled to the patient interface, such as via the shell.

At least the exterior surface of the wall forming the connector 270 preferably tapers along at least part of the length thereof such that at least a portion of the connector 270 nearer the first end 271 has a greater exterior dimension than an exterior dimension of a portion of the connector 27 nearer the second end 272. This tapering refers to the substantially cylindrical body forming the connector 270 and not the rib or projection 273 proximate the first end 271 of the connector 270. Tapering is commonly used for tube connectors and is configured to couple to a respiratory tube or a collar terminating such a tube as would be apparent to those skilled in the art. Additionally or alternatively, tapering may be provided in the inside of the respiratory tube (or collar terminating said tube), the inside of the tube (or collar) narrowing from its mouth. The tapering facilitates insertion of the second end 272 of the connector 270 into the respiratory tube, with a seal being formed on continued insertion thereof.

Figures 23A, 23B:
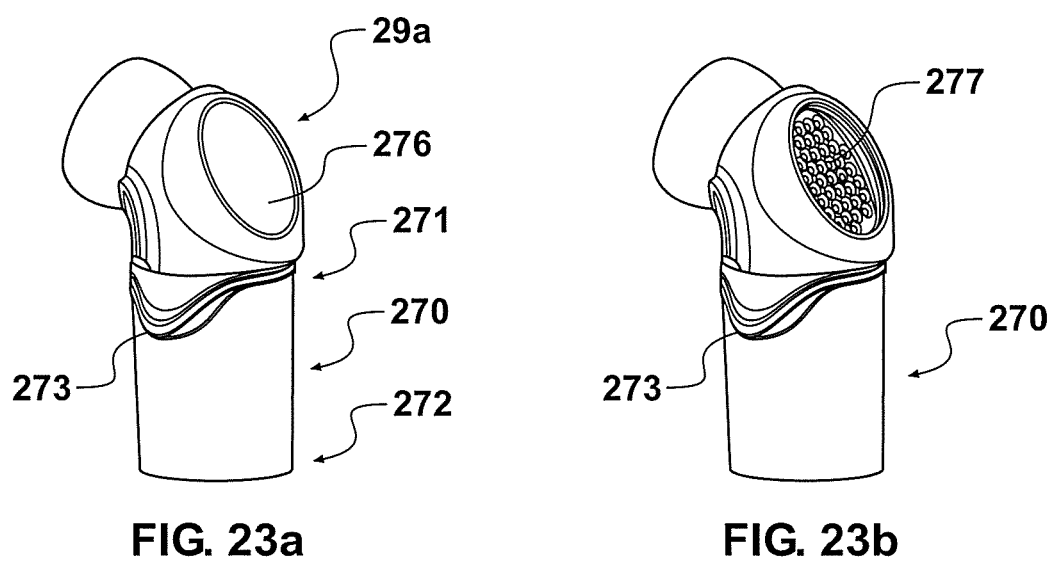
FIG. 23a is a perspective view of a configuration of a connector and elbow assembly.
FIG. 23b is a perspective view of the connector and elbow assembly of FIG. 23a with a portion removed.
Figure 23C:
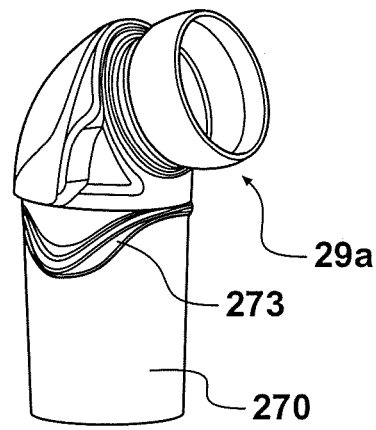
Figure 23D:
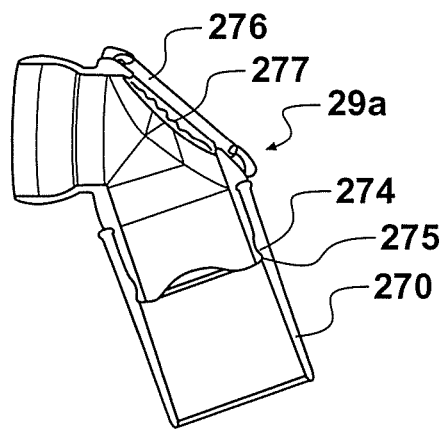
FIG. 23d is a cross-sectional view of the connector and elbow assembly of FIG. 23a FIGS. 24a-24c show side, perspective and alternative perspective views, respectively, of the elbow connector shown in FIGS. 23a-23d.
Figure 24A:
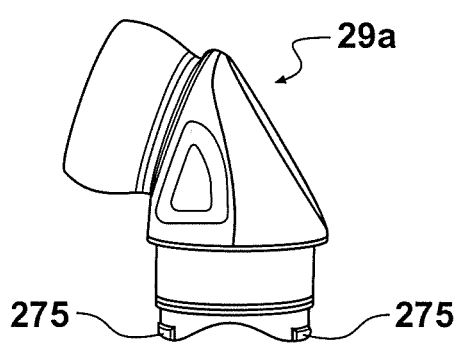
Figure 24B:
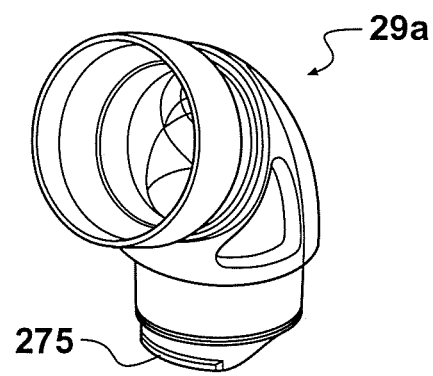
Figure 24C:
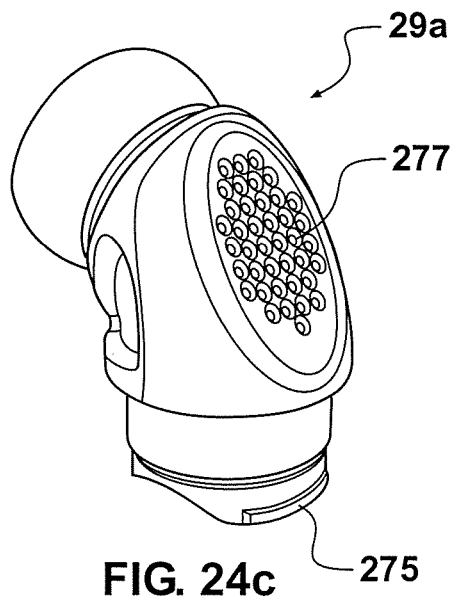
Figure 25A:
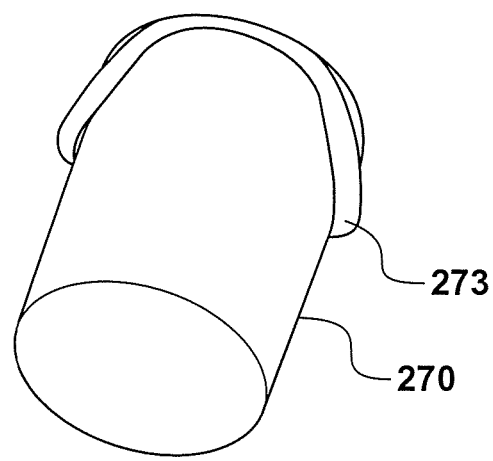
FIGS. 25a-25f show first and second perspective views, a side view, a front view, a cross-sectional view and a top view of the elbow connector shown in FIGS. 23a-23d.
Figure 25B:
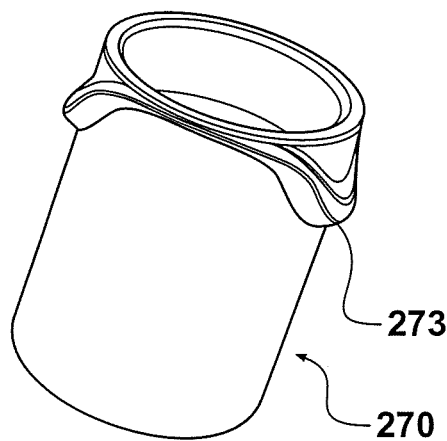
Figure 25C:
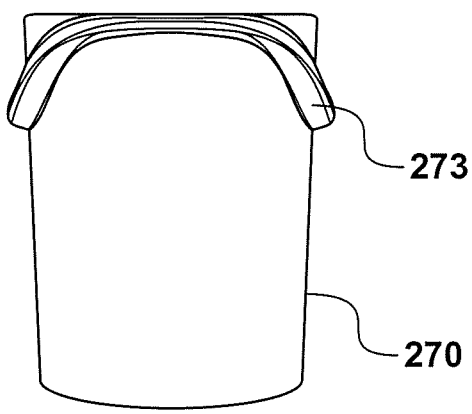
Figure 25D:
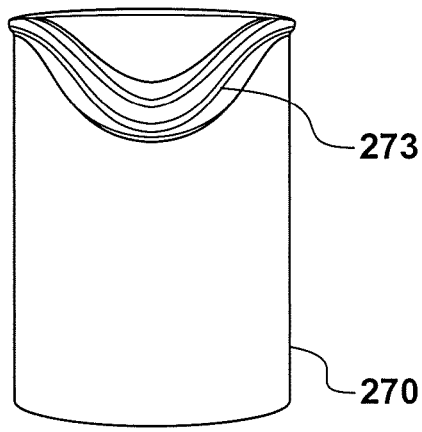
Figure 25E:
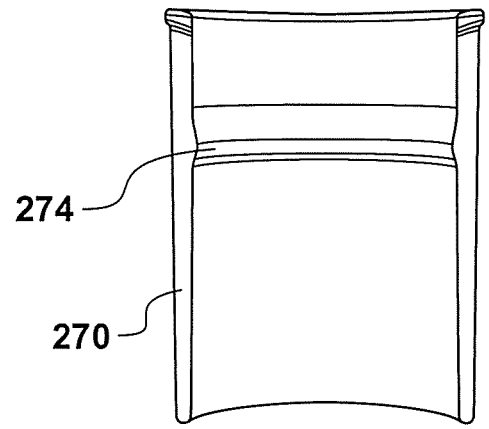
Figure 25F:
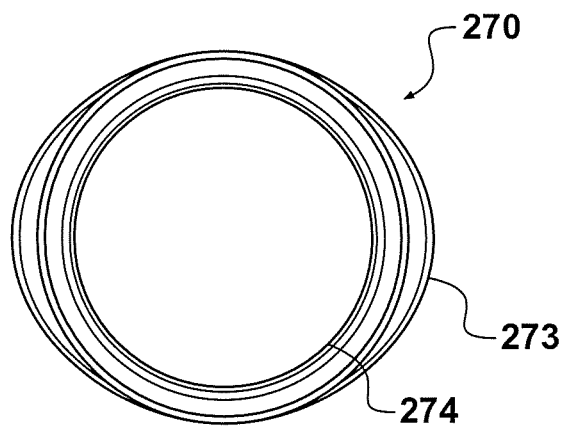
Figure 26:
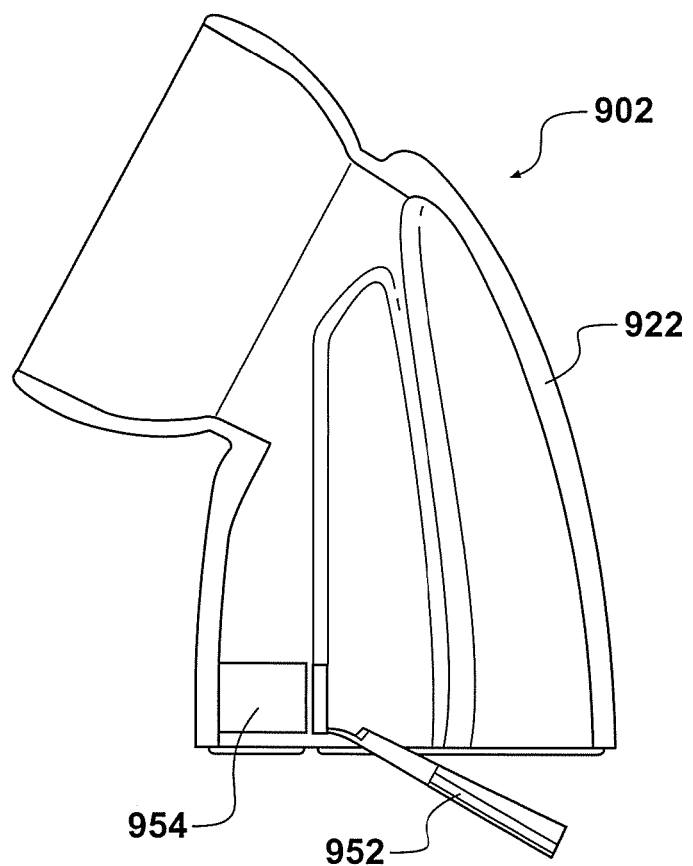
FIG. 26 is a cut-away side view of a conduit connector assembly in the form of an elbow assembly in accordance with the present disclosure incorporating an anti-asphyxia valve.
Figure 27:
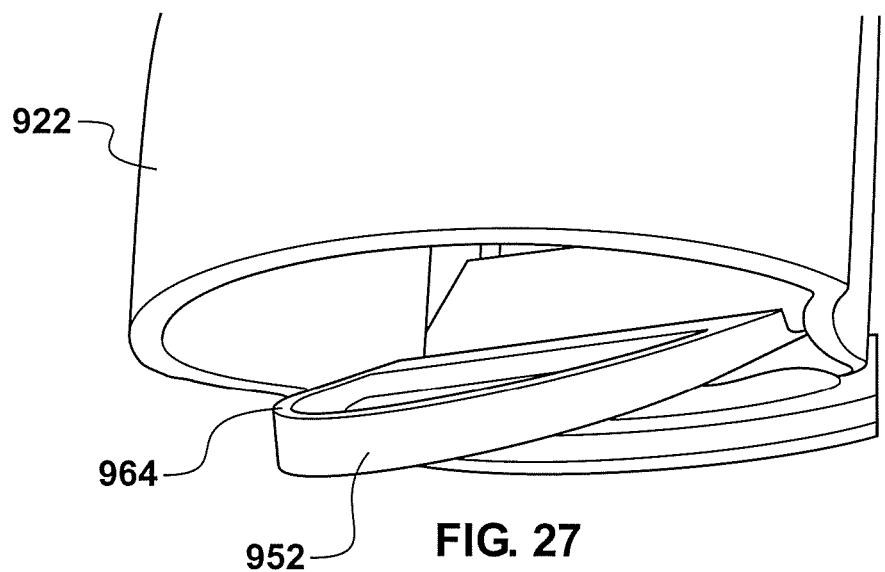
FIG. 27 is an enlarged perspective view from below of the elbow assembly of FIG. 26.

As best seen in FIGS. 23d and 25e, the interior of connector 270 includes a rib 274 which engages one or more projections 275 on elbow connector 29a, forming a click or snap fit. More generally, the elbow connector 29a is substantially the same or similar to the previous elbows connectors disclosed herein and only pertinent features of elbow connector 29a will be described. Note in FIG. 23a, elbow connector 29 is shown including cover 276 while this is omitted from FIG. 23b to expose a plurality of vent holes 277. Cover 276 could be a filter, allowing gases and/or moisture to pass therethrough or may solid and impermeable, so as to block the vent holes 277 when the cover 276 is in place.

The interior of the connector 270 extending from a point towards the second end 272 is preferably dimensioned to prevent engagement of the inside surface of the second end 272 of the connector 270 with the outer surface of the elbow connector 29a in the event a user attempts to incorrectly assemble the components together. In a preferred embodiment, this is realized by the inner dimension (generally diameter) of the connector 270 being greater than the external dimension of the elbow connector 29a that engages with the connector 270, such that it is readily apparent that the two are incorrectly assembled in view of the loose fit therebetween. Alternatively, the second end 272 of the connector 270 could have an inner dimension that prevents insertion of the elbow connector 29a therein i.e. it is too narrow or includes projections that act as stops.

Rib or projection 273 serves two functions. Firstly, it provides a grip for a user's fingers that may be used to remove the connector 270 from engagement with the elbow connector 29a. Secondly, it serves as a mechanical stop, limiting how far a respiratory tube may be pushed onto the second end 272 of the connector 270.

While the illustrated embodiment has the rib or projection 273 arcing in a sinusoidal pattern about the outer circumference of the connector 270 proximate the first end 271, the rib or projection 273 may be otherwise formed. For example, it may only extend part way around the circumference or comprise a number of discrete elements, each of which extends part way around the circumference. Further, the projection or rib may be substantially linear and/or comprise linear portions, in addition to or as an alternative to arcuate portions.

Referring additionally to FIGS. 26 to 31, another embodiment of an elbow assembly 902 comprises an elbow 922 and a sleeve (not shown), with similar features to elbow 722 and sleeve 710 of FIGS. 14 to 19. The swivel 330 as described above may also be provided but is not illustrated in FIGS. 26 to 31.

An anti-asphyxia valve (AA valve) 950 is provided and positioned over the sleeve such that it at least partially obstructs the sleeve's flow channel. AA valve 950 has similar features to valve 750 of FIGS. 14 to 19. The elbow assembly 902 functions similarly to the elbow assembly 302 of FIGS. 10 to 13 and to the elbow assembly of FIGS. 14 to 19, and similarly directs gases away from the patient when the flap 952 of the AA valve 950 drops to its closed position, namely a generally horizontal position, closing the flow channel through the sleeve.

The AA valve 950 comprises generally planar valve flap 952 which is hingedly mounted on a flap support 954 which may be integrally formed with the valve flap 952. In this example, in contrast to the valve flap 752 as shown in FIGS. 14 to 19, the valve flap 952 and the flap support 954 are configured so that at rest the flap 952 is biased downwardly so as to be inclined relative to a notional horizontal plane, that is, inclined downwardly relative to the planar underside of the flap support 954, before the sleeve is assembled on the elbow 922. When the valve 950 is in use, mounted in the elbow 922 with the sleeve in place, the flap 952 is horizontal, with the planar lower surface of the flap 952 flush with, and parallel to, the upper planar sealing surface of the sleeve, as shown in FIG. 14 for example.

During assembly, the sleeve moves the downwardly inclined valve flap 952 upwardly to the generally horizontal position when the sleeve is fully assembled on the elbow 922. When the valve flap 952 is at rest in the generally horizontal position, the flap 952 is trying to pivot downwardly against the sleeve, that is, the flap 952 is biased downwardly, away from the vertical orientation, helping the flap 952 remain in the horizontal orientation with the flow channel through the sleeve closed and the air venting channels in the elbow 922 open. This biased flap 952 helps to ensure that the user of the elbow can still breathe, through the air venting channels in the elbow 922, when breathing gas is not being delivered through the flow channel in the sleeve.

The degree of biasing created by the flap 952 being initially downwardly inclined can be configured by the thickness of the hinge 960 between the flap support 954 and the flap 952, and the size of the angle of the flap 952 relative to the notional horizontal plane (which is parallel with the planar undersurface of the flap support 954) when the flap 952 is in a rest condition, prior to assembly with the sleeve. If the hinge thickness is too great, the flap 952 will not flex sufficiently easily for the flap 952 to pivot about the hinge 960 in the above described manner. If the hinge thickness is too thin, the flap 952 can be unstable in that it flexes, deforms and vibrates too much to perform an effective seal when in the vertical and/or horizontal positions.

In this example, the valve 950 is provided with further features, which features may also be used with the other examples of the valve 350, 750 described herein. One such feature is that in this example, the sealing bead 964 extends around the top surface of the valve flap 952 to form a 'D' shaped seal, as per the sealing bead 964 of valve flap 752. However, at a part of the sealing bead 964 adjacent the flap support 954, the sealing bead 964 comprises a linear bead portion 964a of increased surface area, which seals against the vertical front face 954a of the flap support 954, when the flap 952 is in a vertical orientation. The linear bead portion 964a comprises an oblong, planar sealing face which extends across the flap 952 from one side to the other, adjacent the hinge 960. The width and length of sealing face of the linear bead portion 964a closely corresponds to, or is preferably identical to, the height and width of front face 954a of flap support 954 such that when the flap 952 is in the vertical position, sealing face of the linear bead portion 964a is substantially matched in size and shape with, and seals against, all of front face 954a. This generates an improved seal between the part of the flap 952 that contacts the flap support 954.

A margin of the oblong sealing face of the linear bead portion 964a comprises an inclined, transitional wall 964b where the face of the linear bead portion 964a meets the upper surface 972 of the valve flap 952. The upper surface 972 is defined as a recessed planar region bounded by the sealing bead 964. The thickness of the transitional wall 964b can be configured to control the stiffness of the flap 952, that is, the transitional wall 964b functions as a stiffening rib or reinforcement member. The transitional wall 964b can help prevent the valve flap 952 from ballooning or otherwise flexing and distorting under pressure in use, where otherwise the flap 952, and particularly the upper surface 972, may be too thin to resist the pressures generated in use.

Figure 28A:
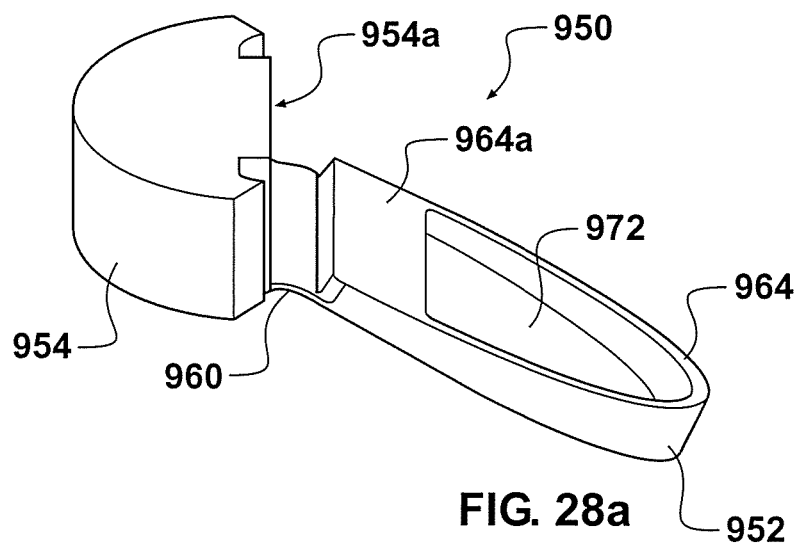
FIGS. 28a-28c show top perspective, side and bottom perspective views of the anti-asphyxia valve of the elbow assembly of FIGS. 26 and 27.
Figure 28B:
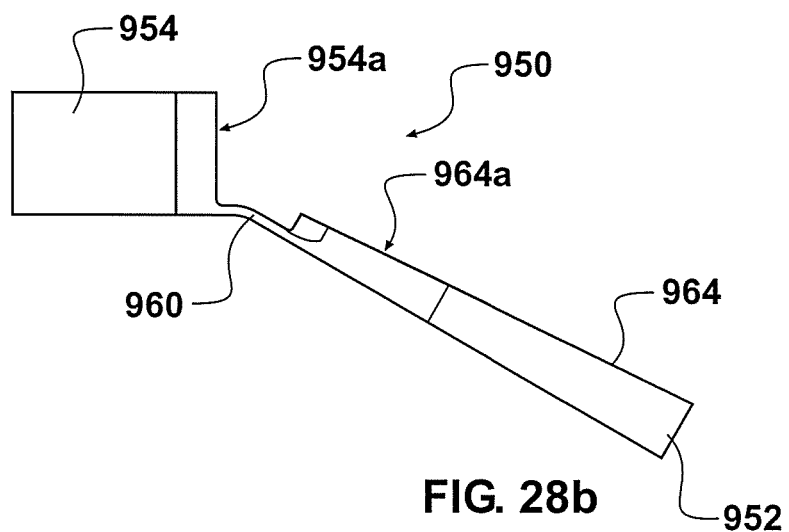
Figure 28C:
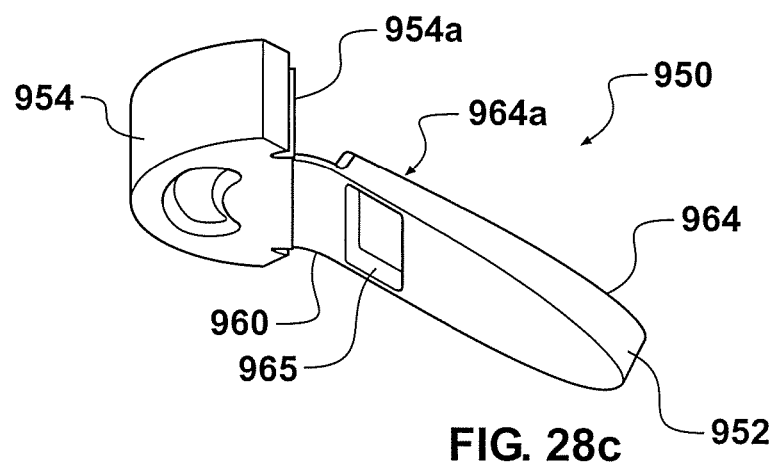
Figure 29:
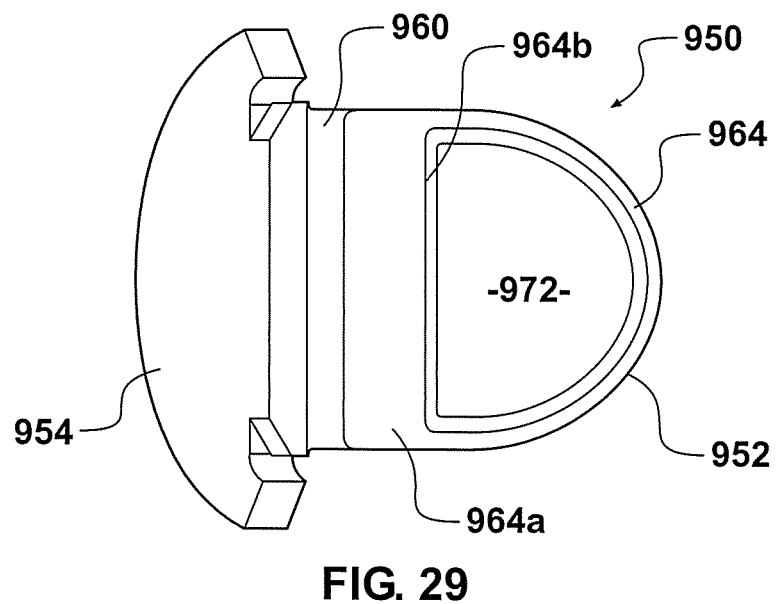
FIG. 29 is a plan view of the valve of FIGS. 26 to 28.
Figure 30:
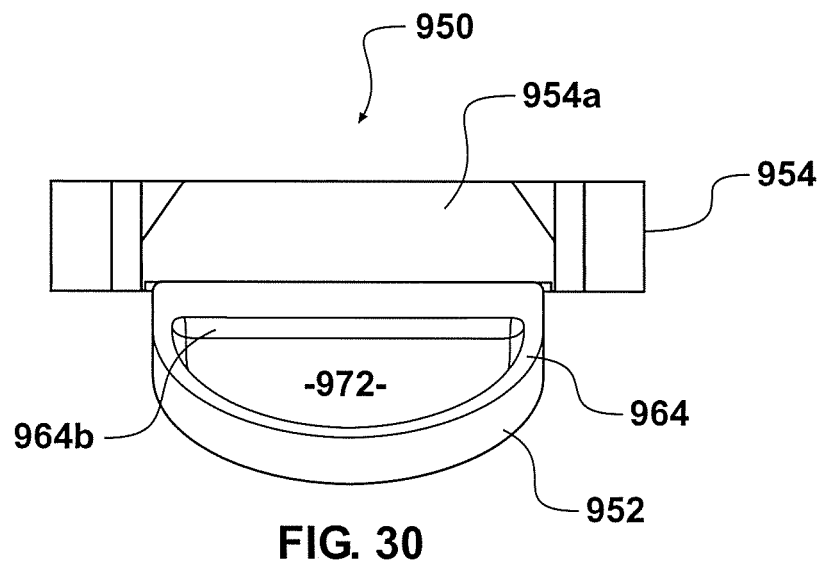
FIG. 30 is a front view of the valve of FIGS. 26 to 29.
Figure 31:
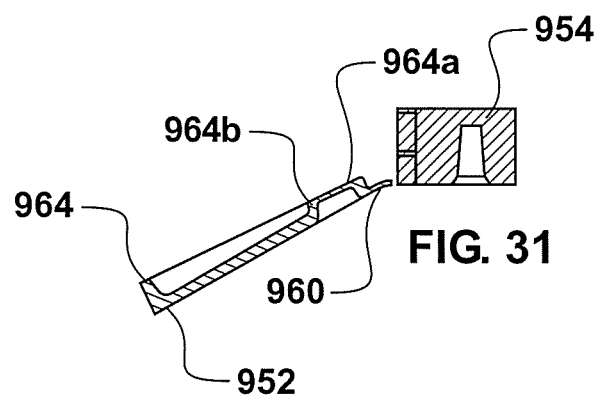
FIG. 31 is a sectional side view of the valve of FIGS. 28 to 30, showing non-limiting, optional example dimensions.

Likewise, and with particular reference to FIG. 28c, the underside of the valve flap 952, adjacent the hinge 960, may comprise a recess 965 configured to allow a desired amount of flex in the valve flap 952, adjacent the hinge 960. Some flex in the valve flap 952 is useful in allowing the flap 952 to deform sufficiently to achieve the best possible seal against the sealing faces of the elbow 922 and sleeve. In this example the recess 965 is oblong, defined directly underneath the upper sealing face of the linear bead portion 964a.

The dimensions and thicknesses of the features of the valve flap 952 and the flap support 954 may be configured as individual parameters, and/or relative to one another, to ensure that the valve flap 952 has the desired properties to achieve the best seal in both the horizontal and vertical positions, and also reacts appropriately to changes in pressure to move effectively from the horizontal to the vertical positions and vice versa. Additional reference is made to FIG. 31, which shows some example and non-limiting dimensions in one embodiment of the valve 950.

The valve 950 may have the following properties, each of which may be provided as an individual feature or in combination with a property of another feature or features:
a) The angle of the flap 952 prior to being assembled between the elbow and sleeve, in particular the angle of the planar undersurface of the flap 952, may be inclined between 0 and 90° from the notional horizontal plane, and is preferably between 0.5 and 75°, more preferably from 5 to 60°, more preferably 5 to 45°, and in one preferred embodiment between 10 and 40°.
  b) The thickness of the hinge 960, when viewed from the side as per FIG. 28*b* for example, may be between 0.05 and 1.0 mm, preferably between 0.1 and 0.75 mm, more preferably between 0.1 and 0.5 mm, more preferably between 0.15 and 0.4 mm, and in one preferred embodiment is 0.25 mm.
  c) The thickness of the flap support 954, when viewed from the side, may be between 1 and 10 mm, preferably between 1 and 7.5 mm, more preferably between 1 and 5 mm, and in one preferred embodiment is 4.75 mm.
  d) The thickness of the valve flap 952 in the region of the upper planar surface 972 between the sealing bead 964, may be between 0.1 and 2 mm, preferably between 0.5 and 1.5 mm, more preferably between 0.5 and 1 mm, and in one preferred embodiment is 0.75 mm. e) The thickness of the inclined, transitional wall 964*b*, when viewed in section from the side, may be between 0.1 and 1.5 mm, preferably between 0.2 and 1 mm, more preferably between 0.2 and 0.75 mm, more preferably between 0.3 and 0.6 mm, and in one preferred embodiment is 0.53 mm.
  f) The thickness of the linear bead portion 964*a* above recess 965, when viewed in section from the side, may be between 0.1 and 1 mm, preferably 0.1 and 0.75 mm, more preferably between 0.1 and 0.5 mm, and in one preferred embodiment is 0.3 mm.
  g) The width of the linear bead portion 964*a*, in a direction away from the hinge axis and away from the flap support 954 when viewed in plan, may be between 2 and 6 mm, preferably 2 and 5 mm, more preferably 3 and 4 mm, and in one preferred embodiment is 3.89 mm.
  h) The length of the valve flap 952 in a direction extending perpendicularly from the hinge 960 to the apex of the valve flap 952 may be between 10 and 25 mm, preferably 10 and 20 mm, more preferably 12 and 18 mm, and in one preferred embodiment is about 15.5 mm. i) The sealing bead 964 preferably tapers towards the hinge 960 so as to be relatively thick distal from the hinge 960 and relatively thin adjacent the hinge 960, when the sealing bead 964 is viewed from the side. The sealing bead 964, and in particular the plane of the upper top surface of the sealing bead 964 may be angled between 0 and 45° relative to the planar undersurface of the flap 952, preferably 0 and 30°, more preferably, 1 and 15°, and in one preferred embodiment is about 4°. The greater the angle, the greater the bead will project into the flow path of the elbow assembly. However, the smaller the angle, the more likely that the flap will undesirably stick in a vertical orientation.
  j) The flap 952, when viewed from above, in the example of FIGS. 26 to 31 is substantially semi-circular or horse-shoe shaped. However, in other embodiments, the flap may be any other desired shape, and may, for example, be substantially square, oblong, triangular, circular or omega shaped, when viewed in plan.

In accordance with the disclosure, the following ratios of properties of features of the valve 950, may be varied as follows:
  a) Flap support 954 thickness to hinge 960 thickness: may be between 5:1 and 30:1, more preferably 10:1 to 25:1, more preferably 15:1 to 25:1, and in one preferred embodiment 19:1.
  b) Valve flap 952 thickness in the region of upper planar surface 972 between the bead to hinge 960 thickness: may be between 1:1 and 10:1, more preferably 1:1 to 8:1, more preferably 2:1 to 5:1, and in one preferred embodiment 3:1.
  c) Valve flap 952 thickness in the region of upper planar surface 972 between the bead to the thickness of the linear bead portion 964*a* above recess 965: may be between 1:1 and 10:1, more preferably 1:1 to 8:1, more preferably 2:1 to 5:1, and in one preferred embodiment 2.5:1. d) Valve flap 952 thickness in the region of upper planar surface 972 between the bead to thickness of the inclined, transitional wall 964*b*: may be between 1:1 and 10:1, more preferably 1:1 to 5:1, more preferably 1:1 to 2:1, and in one preferred embodiment 1.4:1.
  e) Valve flap 952 thickness in the region of upper planar surface 972 between the bead to thickness of the linear bead portion 964*a* above recess 965: may be between 1:1 and 10:1, more preferably 1:1 to 5:1, more preferably 2:1 to 3:1, and in one preferred embodiment 2.5:1. F) Thickness of the inclined, transitional wall 964*b* to the thickness of the linear bead portion 964*a* above recess 965: may be between 1:1 and 10:1, more preferably 1:1 to 5:1, more preferably 1:1 to 2:1, and in one preferred embodiment 1.75:1. g) Flap support 954 thickness to the width of linear bead portion 964*a*: may be between 1:1 and 10:1, more preferably 1:1 to 5:1, more preferably 1:1 to 2:1, and in one preferred embodiment 1.2:1. h) Width of linear bead portion 964*a* to thickness of the linear bead portion 964*a* above recess 965: may be between 1:1 and 30:1, more preferably 1:1 to 20:1, more preferably 1:1 to 15:1, and in one preferred embodiment 13:1.

Figure 32:
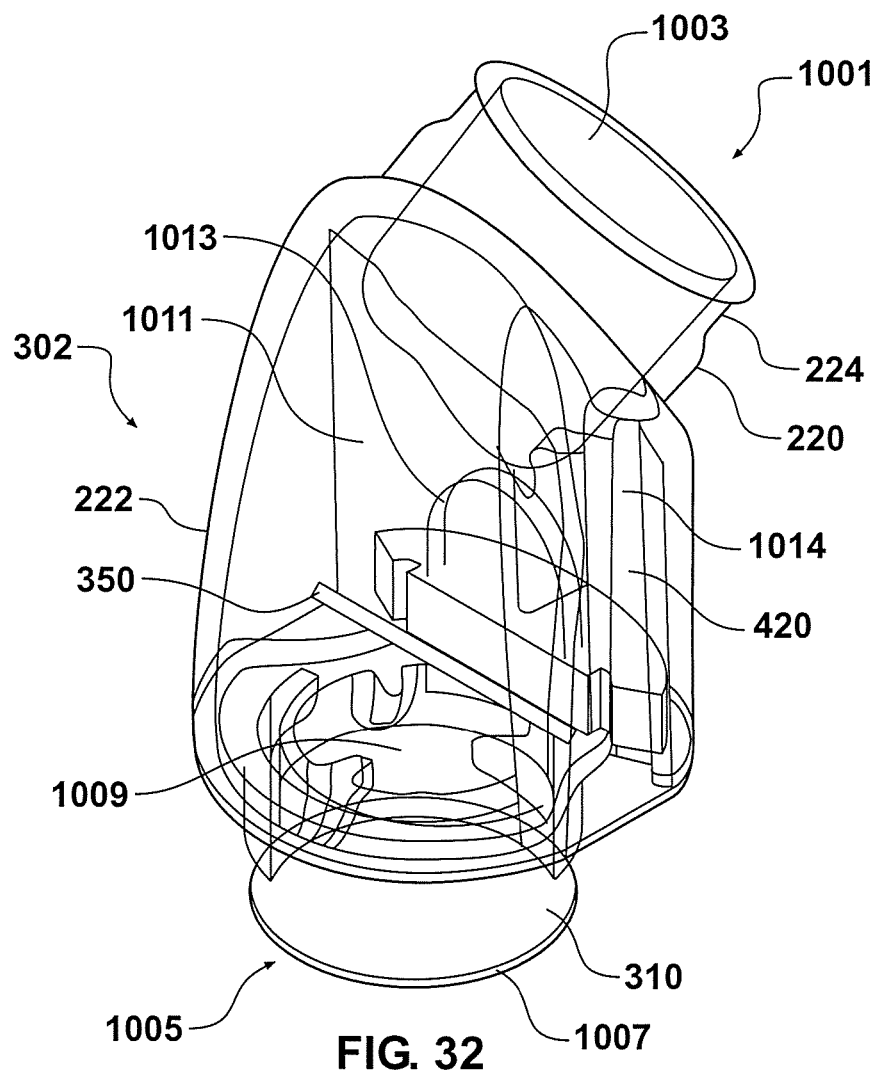
FIG. 32 is a side view of another configuration of a conduit connector assembly in the form of an elbow assembly.

FIG. 32 shows another view of the elbow assembly 302 of FIGS. 10-13. The elbow assembly 302 comprises an elbow 222, a sleeve 310, and/or a swivel 330, as shown in FIG. 11. The elbow 222 comprises first and second ends adjacent mask assembly 102 and the gas delivery conduit respectively. In some configurations, the elbow assembly 302 only includes the elbow 222 and sleeve 310 and omits the swivel 330. The swivel 330 may be permanently or removably attached to the sleeve 310 and elbow 222. In some configurations, the swivel 330 is integrally formed with the end of the gas delivery conduit. A swivel connector is provided between the elbow 222 and the mask assembly 102, which in this example comprises a ball end 220 of elbow 222, the ball end 220 having a contoured surface 224 that can be snap fit into the contoured surface 214 formed in the mask base 114. An anti-asphyxia valve flap 350 is positioned over the sleeve 310 such that it at least partially obstructs the sleeve's flow channel 352

The elbow 222 comprises a first end 1001 which comprises the swivel connector and a first flow port 1003 configured to be connected to the patient interface 100, and a second end 1005 comprising a second flow port 1007 configured to be connected to the gas delivery conduit via a flow channel 1009 extending through the elbow 222 between the first and second ends 1001, 1005.

As can be more clearly seen in FIG. 32, the interior of the elbow 222 is divided by an interior dividing wall 1011. The flow channel 1009 is defined on one side of the dividing wall 1011. The dividing wall 1011 is provided with a valve opening 1013 which is closed and opened by the anti-asphyxia valve flap 350. The valve opening 1013 is in fluid communication with a chamber 1014 on the other side of the dividing wall 1011 from the flow channel 1009, the chamber 1014 being in communication with the expiratory flow ports 420.

Figure 33A:
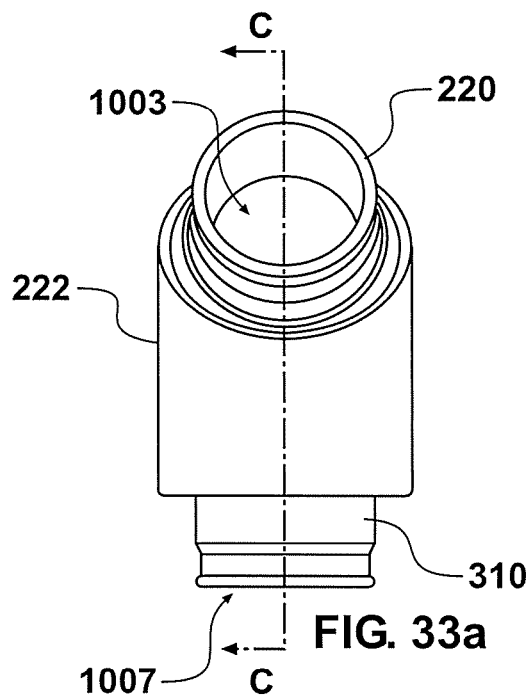
FIGS. 33a-c are, respectively, rear, sectional side and part enlarged views of another configuration of an elbow assembly.
Figure 33B:
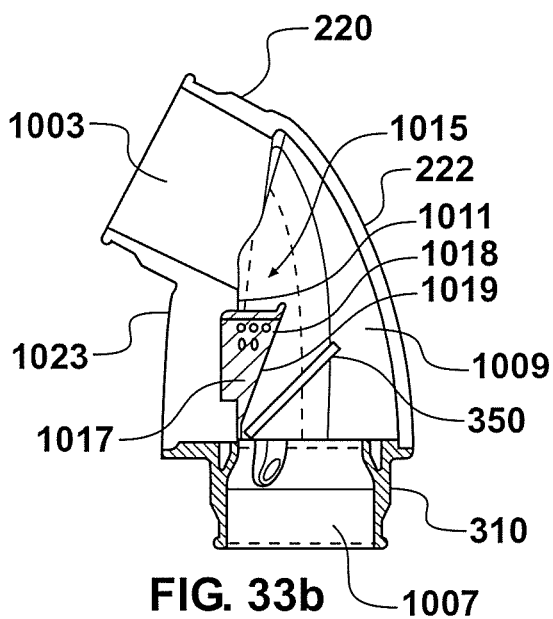
Figure 33C:
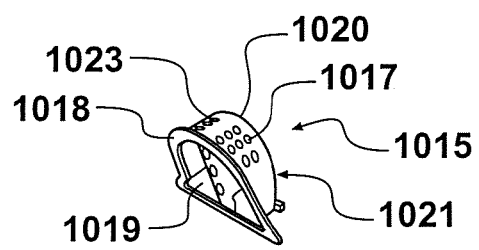
Figure 34:
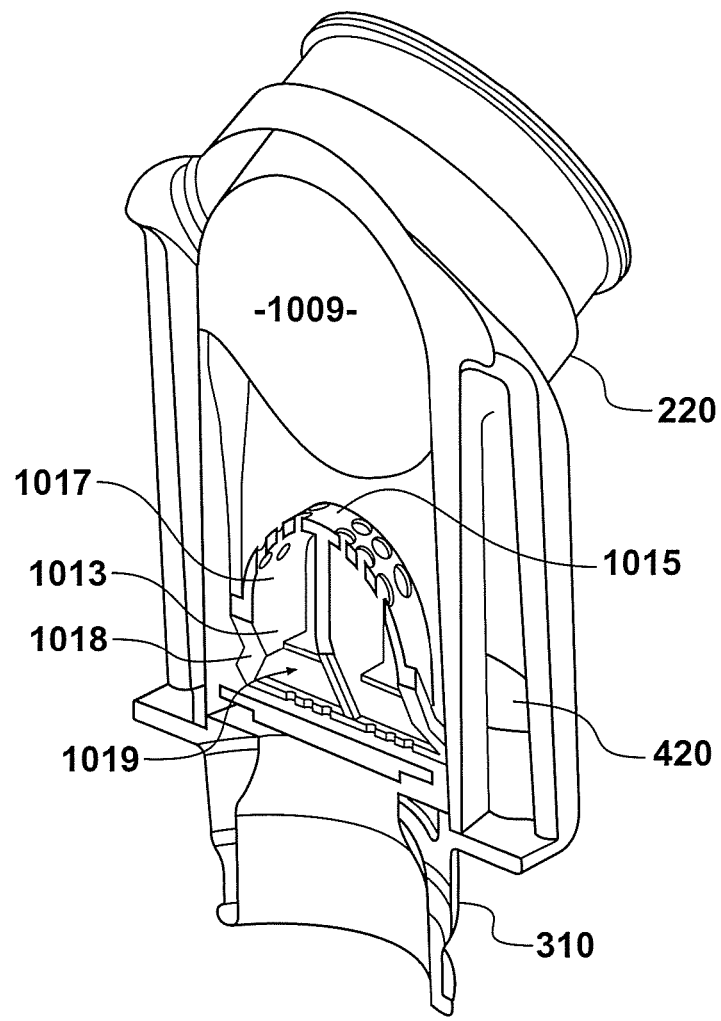
FIG. 34 is a sectional view of the elbow assembly of FIG. 33.

Referring additionally to FIGS. 33 and 34, a gas flow directing structure 1015 is provided comprising a valve body 1017 configured to be mounted on the valve opening 1013 on dividing wall 1011. The valve body 1017 is generally tubular and comprises a first, planar end face 1018 which projects into the flow channel 1009 and which is inclined relative to a longitudinal axis of the valve body 1017, and defines a first valve port 1019. The valve body 1017 further comprises an opposed planar end face 1020 which is perpendicular to the longitudinal axis of the valve body 1017 and defines a second valve port 1021. Second valve port 1021 is configured to be mounted on, and to abut, the valve opening 1013. The valve body 1017 is therefore wedge shaped at one end, with the wedge projecting into the flow channel 1009. Valve body 1017 further comprises a third valve port 1023, which in this example comprises an array of valve ports on a side wall of the valve body 1017 between the first and second valve ports 1019 and 1021.

In use, the valve flap 350 is movable between a first position, wherein the flap 350 at least partially blocks the first valve port 1019 and allows inspiratory gas from the gas delivery conduit to pass to a user via the elbow 222, and
   a second position, wherein the flap 350 at least partially blocks the gas delivery conduit thereby allowing expiratory gas to flow from the user into the valve body 1017 via the first valve port 1019 and to the expiratory flow ports 420 via the second valve port 1021.

The third valve port 1023 forms a supplementary gas flow path between the elbow flow channel 1009 and the expiratory flow ports 420. This supplementary gas flow path remains permanently open regardless of the position of the valve flap 350, and allows air to be drawn into the flow channel 1009 of the elbow 222 through the expiratory flow ports 420 during inspiration, and air to be expelled from flow channel 1009 through expiratory flow ports 420 during expiration. Thus the valve body 1017 forms part of the expiratory flow path when the system is pressurized, that is, when a pressurized flow of inspiratory gas enters elbow 222 via the gas delivery conduit.

Figure 35A:
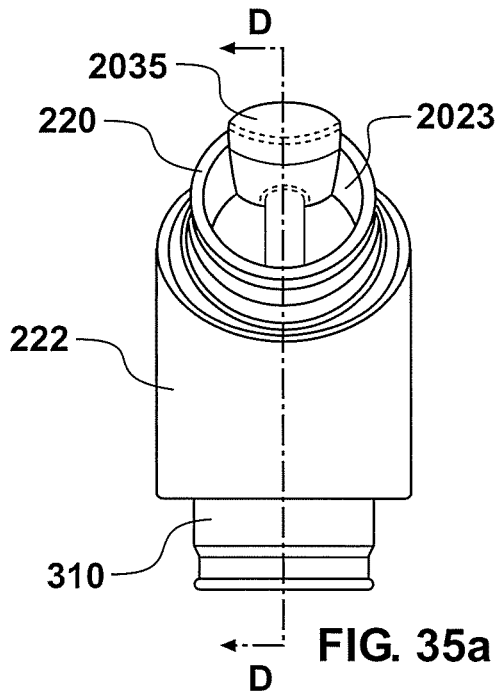
FIGS. 35a-c are, respectively, rear, sectional side and part enlarged views of another configuration of an elbow assembly.
Figure 35B:
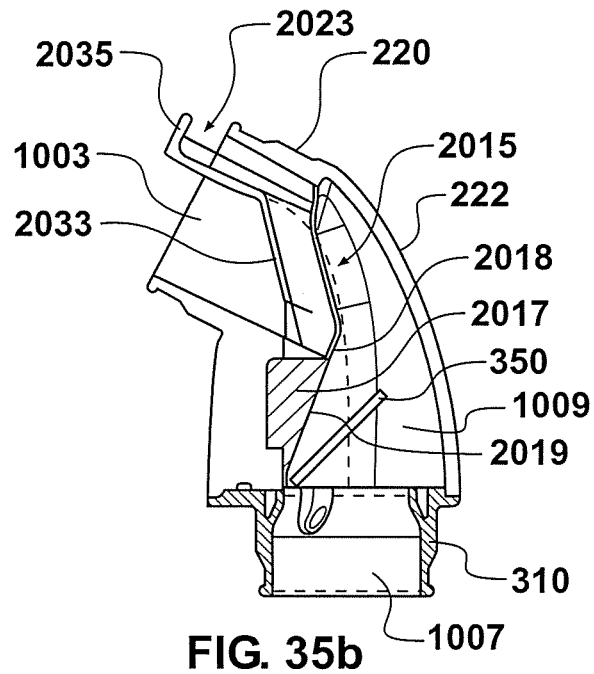
Figure 35C:
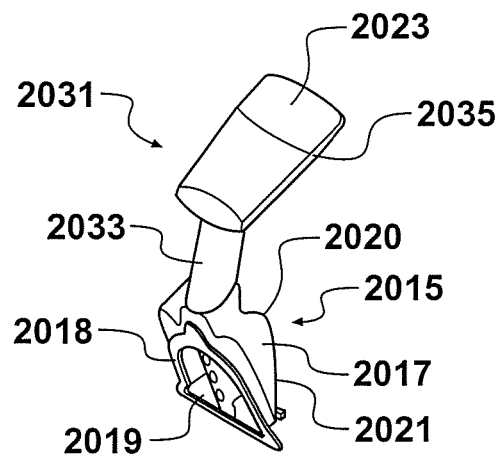
Figure 36:
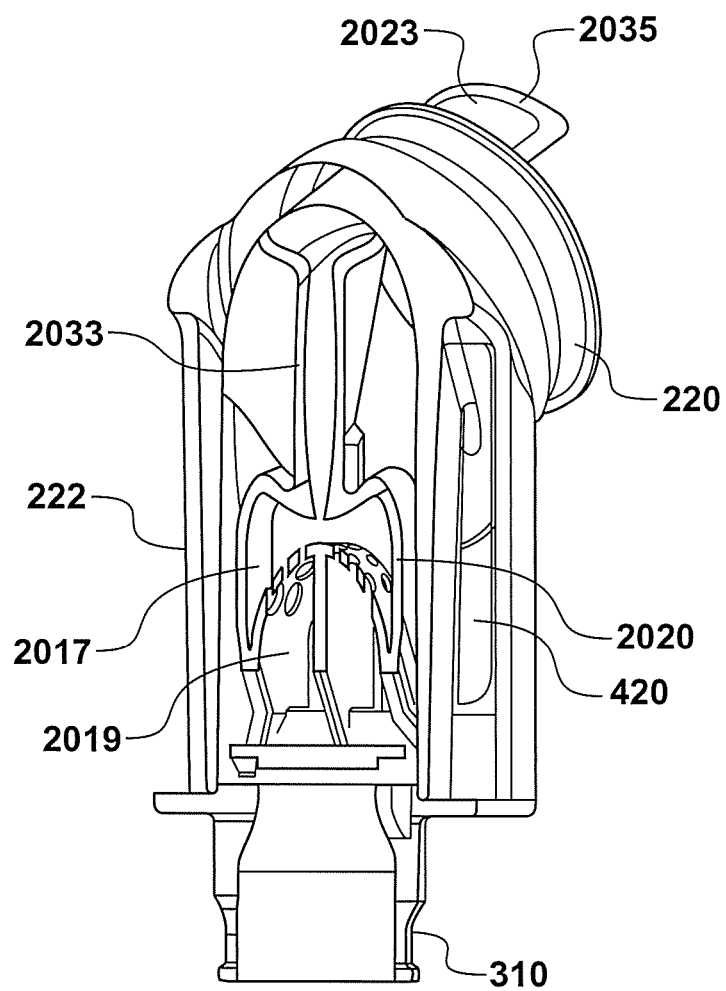
FIG. 36 is a sectional view of the elbow assembly of FIG. 35.

Referring additionally to FIGS. 35 and 36, another gas flow directing structure 2015 is provided comprising a valve body 2017 configured to be mounted on the valve opening 1013 on dividing wall 1011. The valve body 2017 is generally tubular and comprises a first planar end face 2018 which projects into the flow channel 1009 and which is inclined relative to a longitudinal axis of the valve body 2017, and defines a first valve port 2019. The valve body 2017 further comprises an opposed end face 2020 which is perpendicular to the longitudinal axis of the valve body 2017 and defines a second valve port 2021. Second valve port 2021 is configured to be mounted on, and to abut, the valve opening 1013. The valve body 2017 is therefore wedge shaped at one end, with the wedge projecting into the flow channel 1009.

Gas flow directing structure 2015 further comprises a snorkel arrangement 2031 depending from, and in communication with the interior of, valve body 2017. The snorkel arrangement 2031 comprises a first relatively narrow diameter tubular portion 2033 which projects upwardly from valve body 2017 and into the flow channel 1009. Tubular portion 2033 merges into an outwardly flared mouth portion 2035 adjacent first end 1001 of the elbow 222. The mouth portion 2035 in this example projects beyond first end 1001 of the elbow 222 and comprises a third valve port 2023 between the first and second valve ports 2019 and 2021. The narrow diameter tubular portion 2033 is relatively narrow so as to be relatively streamlined so that inspiratory gas flow can pass around it relatively easily. In other examples the mouth portion 2035 may terminate flush with the first end of elbow 222, or at a position inside the flow channel 1009, spaced from the first end of elbow 222.

The gas flow directing structure 2015 functions in a similar manner to gas flow directing structure 1015 except that the tubular portion 2033 and mouth portion 2035 together form a supplementary gas flow duct 2037 contained within, but separate from the flow channel 1009 through elbow 222. The supplementary gas flow duct 2037 can carry inspiratory air from the external environment to the patient, or carry expiratory gases from the patient, regardless of the position of the valve flap 350.

The inclined front face 1018, 2018 of valve body 1017, 2017 may comprise a plate face provided with an array of vent holes which together form the first valve port 1019, 2019. Likewise the perpendicular opposed face 1020, 2020 of valve body 1017, 2017 may comprise a plate face provided with an array of vent holes which together form the second valve port 1021, 2021.

Figure 38:
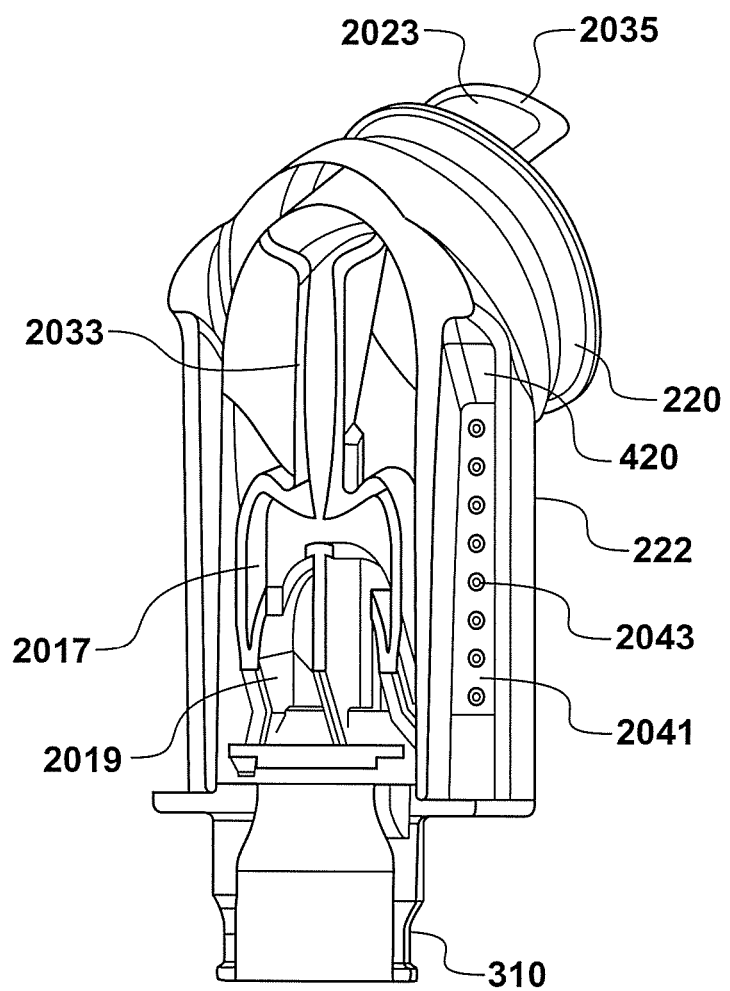
FIG. 38 is a sectional view of the elbow assembly of FIG. 37.

Referring additionally to FIGS. 37 and 38, a modified embodiment of gas flow directing structure 2015 comprises diffuser plates 2041 which are shaped and dimensioned to fit in, and to cover, expiratory flow ports 420 in elbow 222. Each diffuser plate 2041 is provided with an array of multiple diffuser vent holes 2043 which extend along the length of the expiratory flow ports 420.

The elbow assembly incorporating elbow 222 having first and second ends 1001, 1005, and expiratory flow ports 420, may comprise part of a common elbow assembly that can be configured differently depending on the function(s) to which the elbow assembly is put. The provision of the internal dividing wall and valve opening is such that different gas flow directing structures can be removably mounted in or at second end of elbow 222. One such gas flow directing structure may comprise an anti-asphyxia valve assembly comprising an anti-asphyxia valve flap as described above with reference to any of FIGS. 8 to 31. Another such gas flow directing structure may comprise an anti-asphyxia valve assembly comprising a valve body which provides a supplementary flow duct through the flow channel of the elbow 222, as described above with reference to any of FIGS. 33 to 38.

The elbow assembly comprising a common elbow housing may be supplied in, or with, a kit with a plurality of different flow directing structures, allowing the common elbow housing to be used for different types of respiratory therapy, depending on the type of flow directing structure with which the elbow is used. For example, a flow directing structure incorporating a supplementary flow duct may be useful in non-invasive ventilation (NIV) therapy where a permanent vent path is required somewhere along the breathing circuit. Such an arrangement may enable NIV therapy to be provided using a breathing circuit comprising only one limb, that is, using only one gas delivery conduit, rather than requiring two limbs, that is, an inspiratory conduit and an expiratory conduit as with prior art arrangements. Single limb NIV can therefore be provided without requiring any additional vents being provided elsewhere in the breathing circuit. Further, the use of a common elbow assembly may have cost saving advantages, both during manufacture and for the end user, and can allow a single elbow assembly, with a common look and feel, to be used for multiple different therapies. Such a common elbow assembly may also make it easier for therapy providers to configure the apparatus, by incorporating the desired gas directing structure, to provide one or other therapy as required.

Figure 39A:
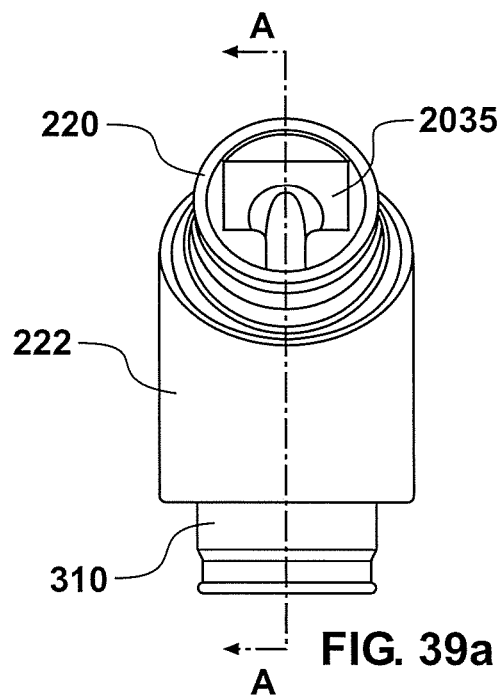
FIGS. 39a-c are, respectively, rear, sectional side and part enlarged views of another configuration of a conduit connector assembly in the form of an elbow assembly.
Figure 39B:
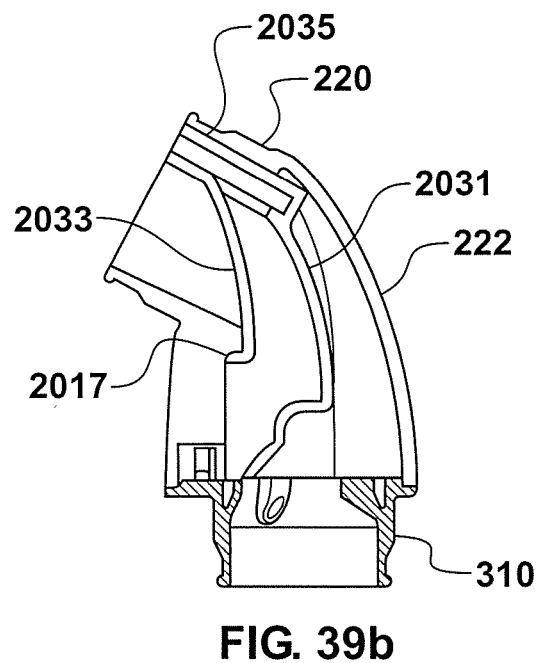
Figure 39C:
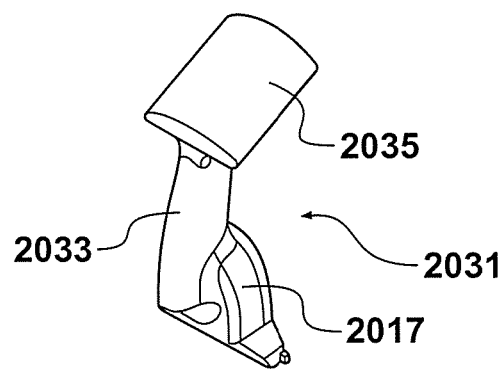
Figure 41:
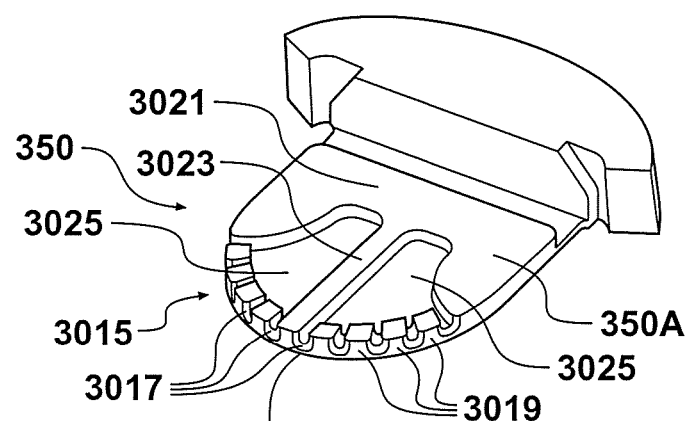
FIG. 41 is a perspective view of a valve flap of another configuration of a conduit connector assembly in the form of an elbow assembly.
Figure 42:
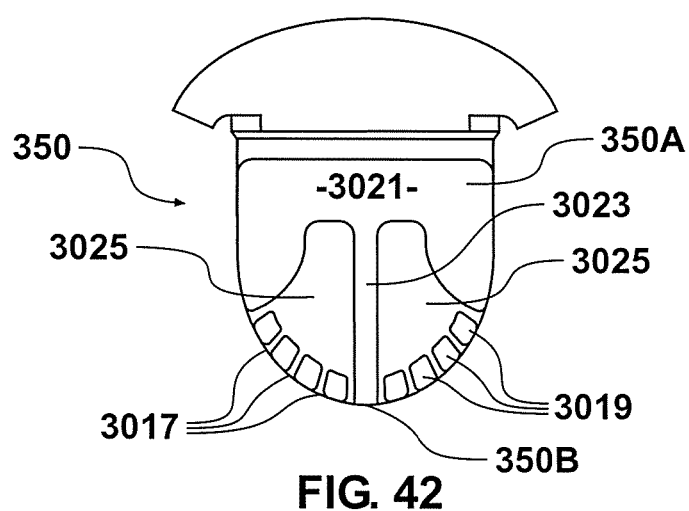
FIG. 42 is a plan view of the valve flap of FIG. 41.
Figure 43:
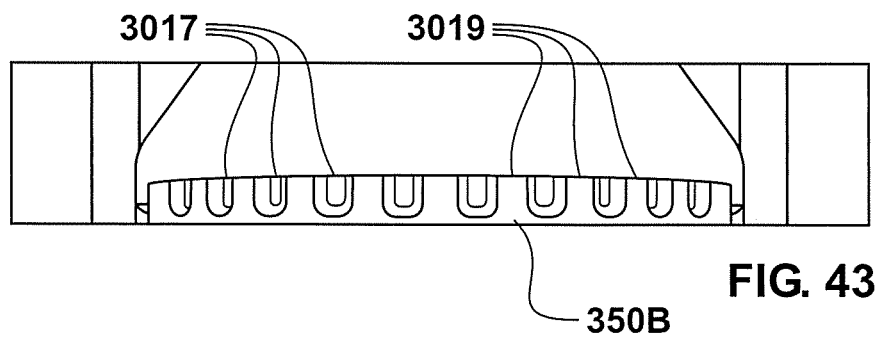
FIG. 43 is a front view of the valve flap of FIG. 41.
Figure 44:
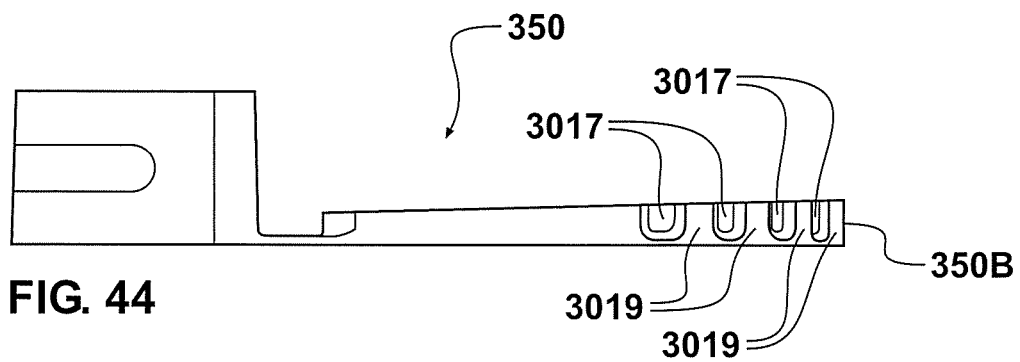
FIG. 44 is a side view of the valve flap of FIG. 41.

The supplementary gas flow duct has been described above as comprising part of, or being used in conjunction with, an anti-asphyxiation valve assembly. However, it is also envisaged that such a duct could be provided without a valve assembly, as shown in FIG. 39 in which snorkel arrangement 2031 is mounted directly on valve opening 1013 of dividing wall 1011, without a valve. In such an arrangement at the least a permanent supplementary flow duct is provided to vent the breathing circuit. Likewise, in the arrangement of FIG. 40, a supplementary gas flow path is provided via the array of apertures 2051 provided in a cap 2053 which mounts on valve opening 2013 in elbow 222. Cap 2053 is provided with alignment lugs or fingers 2055 which engage part of the periphery of the valve opening 2013 to mount the cap 2053 to the dividing wall 2011.

Referring to FIGS. 41 to 56 embodiments are disclosed in which the supplementary gas flow path between the elbow flow channel 1009 and the expiratory flow ports 420 is provided via a gas flow directing structure provided on, or comprising an integral part of, the valve flap 350. These embodiments permit modifications to be made to a conduit connector assembly, such as an elbow assembly as per FIG. 11, whilst minimizing the amount of tooling changes required from an elbow assembly of the type shown in FIG. 11. In these embodiments, the valve body 1017 is not required, with venting via the supplementary flow path being achieved via a vent path defined by a supplementary valve port on, or comprising part of, the valve flap 350 itself.

In these embodiments, by modifying the valve flap 350, an intentional leak path can be created to allow exhaled air to flow from the internal cavity of the elbow 222, through or via the existing flap 350, and out through the expiratory flow ports 420 of the elbow 222 into the ambient environment—thus achieving bias vent flow. This can be achieved by only modifying the tooling for the silicone valve flap 350, without further components being required. For example, any one or more of the following aspects of the AA valve flap can be modified:
 a) the upper or lower face/surface
 b) the overall shape when viewed from above, below, and/or from the side
 c) the contours/profile of the upper or lower face/surface A benefit of these embodiments is that because the valve flap is relatively well concealed within the elbow assembly, it is less likely for the nurses/caregiver to accidentally block any venting from the elbow 222. Aesthetic acceptance and/or patient compliance may also be improved because it appears to the user that no changes have been made to existing patient interfaces with which they are already comfortable/compliant with.

Referring to FIGS. 41 to 45, an upper surface 350A of valve flap 350 comprises a gas flow directing structure 3015 comprising a plurality of vent slots 3017 defined between adjacent blocks or castellations 3019. In this example, when viewed from above, the upper surface 350A comprises a generally T shaped raised region 3021 having a central column 3023 and a pair of recessed regions 3025 distal from the valve hinge or pivot. The blocks or castellations 3019 project upwardly from the recessed regions 3025. The plurality of slots 3017 fluidly couple the recessed regions 3025 to the perimeter 350B of the flap 350.

When a flow of pressurized gas is travelling through the elbow 222 and into the patient interface, the flap 350 is sealingly pressed against the elbow 222 with the recessed regions 3025 in fluid communication with the external ambient environment. In this position the slots 3017 in combination with the elbow 222 create a four walled leak path through which flow can travel from the internal cavity of the elbow 3009, through the slots 3017, into the recessed regions 3025 of the flap 350 and out into the ambient environment.

In this example ten 0.5 mm wide slots 3017 are provided each with a 0.3 mm radius fillet on the external surfaces of the slots 3017 to allow the exhaled air to pass over a smooth surface which minimises the noise generated. The slots 3017 form a U shaped flow path through the AA flap 350 such that the top edges of the U shaped slots 3017 are configured to seal against the elbow housing to form an enclosed flow path through the AA flap 350.

Figure 57:
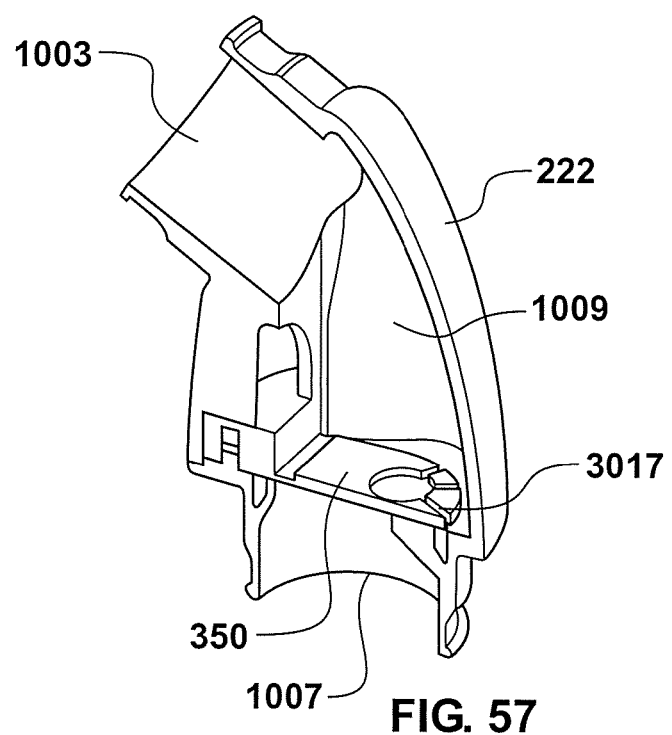
FIG. 57 is a cut-away perspective view of another configuration of a conduit connector assembly in the form of an elbow assembly with a valve flap in a first position.

Having the slots 3017 run laterally through the thickness of the flap 350, that is, to provide a vent flow path substantially parallel with the upper valve surface 350A, as opposed to apertures extending vertically through the flap 350, still allows the flap 350 to form a seal against the elbow housing in the closed position and prevent the patient from breathing up and down the breathing circuit under single fault conditions (loss of pressure supplied to the patient). The closed position can be seen with reference to FIG. 57. In the orientation shown, the valve flap 350 is substantially horizontal, closing off any gas flow to/from the breathing gas delivery conduit (not shown). With the valve flap 350 in this condition, rebreathing of gas (in the event the gas supply through the gas delivery conduit stops) is prevented, with the user able to breath gas from the external environment through expiratory flow ports 420. Consequently, as can be seen via inclined sealing surface 3027 in FIG. 44, the flap 350 can still function as an anti-asphyxia valve, as well as providing the supplementary gas flow path when required.

Figure 45:
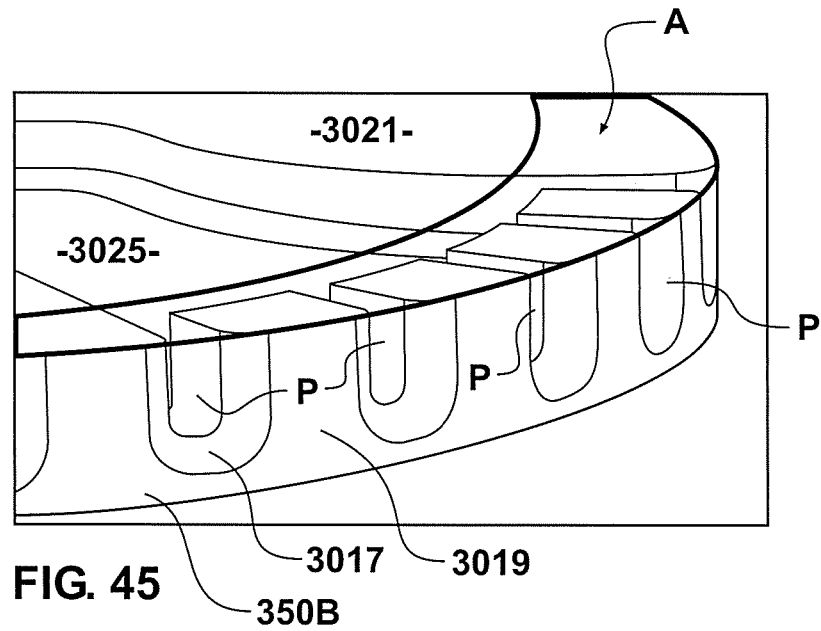
FIG. 45 is an enlarged perspective view of part of the valve flap of FIG. 41.

FIG. 45 is a close up view of the exit point of the slots or channels 3017 each with the radius fillet to reduce noise generated by the flow of exhaled gas exiting the mask. An approximation of the area A that contacts and seals with the elbow 222 is highlighted for reference: this forms an enclosed four walled leak path P that is located between the three walls of the slots 3017 and the elbow 222. A standard AA valve flap would seal the internal cavity of the elbow and prevent communication with the outside environment. However, with the slots 3017 formed in the AA flap 350, exhaled air inside the elbow is able to be vented to atmosphere to achieve the desired bias flow.

The slots 3017 in this example give a desired leak rate of approx. 16 L/min at 4 cmH20. The number, size, shape and/or dimensions of the slots 3017 could be adjusted to achieve any desired leak rate. Elbows with pre-determined leak rates could be manufactured and distributed as single items, coupled to the masks, or be available in packs comprising multiple elbows of varying leak rates, that is, a pack or kit of elbows could be provided with each elbow having a valve flap 350 configured to provide a supplementary gas flow path of a different leak rate.

In this example, each slot 3017 is tapered towards the centre of the valve flap 350 in order to slow the velocity of the exhaled gas. In doing so, the overall noise level of the exhaled gas may decrease. One, some or all of the slots 3017 may taper in either direction, or both, to enable various transformations of the flow of air, for example, slowing velocity, increasing velocity, reducing turbulence, increasing turbulence.

Splitting the recessed region in the flap 350 into two recessed regions 3025 with the central column 3023 separating the two, provides the valve flap 350 with some reinforcing structure to prevent it from deforming under load from the pressure within the elbow and 'falling through' the aperture of the elbow—the flap 350 can pivot between closed and open positions without the flap 350 collapsing.

The length of the slots 3017 can represent the overlap of silicone on the valve to the polycarbonate on the elbow. This overlap could be increased (through changing the design of the elbow or flap 350) such that the exhaled air would travel down a longer silicone tunnel before exiting into the aperture of the elbow. In doing so, the noise and draft of the gas could be further reduced.

Figure 46:
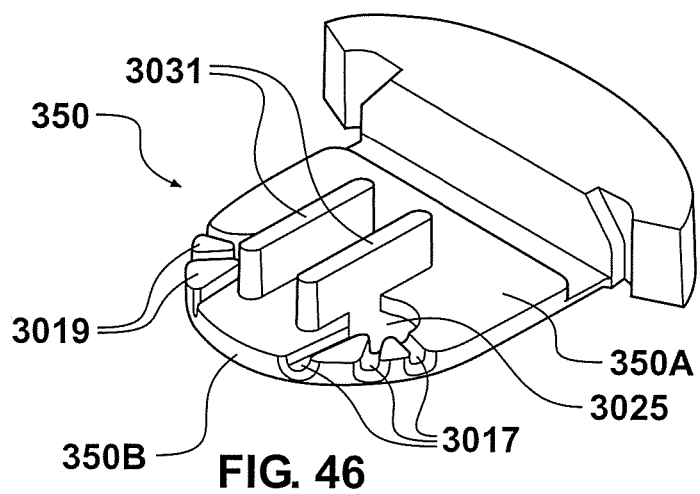
FIG. 46 is a perspective view of a valve flap of another configuration of a conduit connector assembly in the form of an elbow assembly.
Figure 47:
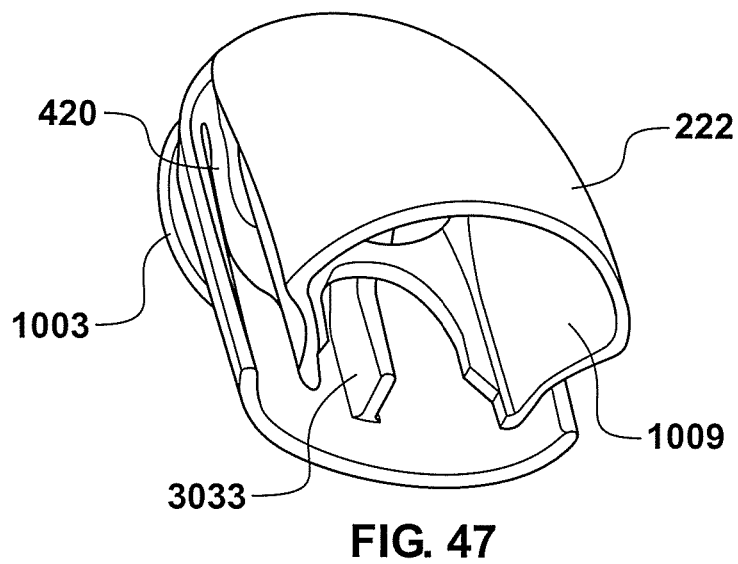
FIG. 47 is a perspective view of an elbow of the elbow assembly of FIG. 46.

With reference to FIGS. 46 and 47, another embodiment of a valve flap 350 provided with supplementary valve ports is shown. In this embodiment the flap 350 comprises six slots 3017 each with an example width of 0.75 mm. This increased width of each slot 3017 provides this embodiment with the same leak rate (same total cross sectional area of slots) as the ten slots 3017 of the example of FIGS. 41 to 45. This shows that the leak rate can be tuned through the amount of cross sectional area that makes up the bias flow path.

This embodiment further comprises two upright stands 3031 or lugs which are configured to further reduce the sound level. Without the stands 3031, the exhaled air can catch a rigid AA valve support structure 3033 in the elbow 222 and the resultant turbulence generated can cause excess noise. The two stands 3031 on the flap are configured to be located in use on either side of this support structure 3033 when the valve flap 350 is in the open position, preventing the exhaled gas from flowing over the support structure 3033. The stands 3031 thus function as flow deflectors or flow restrictors to minimize unwanted flow across a certain part or parts of the elbow 222.

In this example, each recessed region 3025 is relatively small, and located adjacent, and radially outward of, a respective stand 3031.

Figure 48:
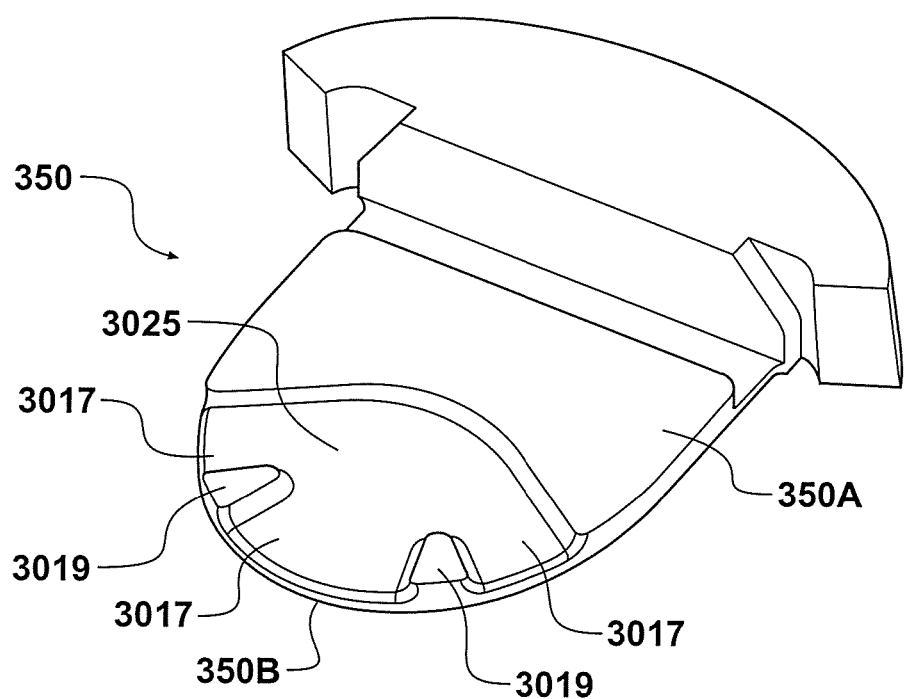
FIG. 48 is a perspective view of a valve flap of another configuration of a conduit connector assembly in the form of an elbow assembly.

Referring now to FIG. 48, the valve flap 350 is modified such that the plurality of smaller slots 3017 of the embodiment of FIGS. 41 to 45 have been replaced with three relatively wide slots 3017 and a single recessed region 3025 which is approximately elliptical when viewed in plan. The relatively large flow paths through each slot 3017 increase the available leak rate as well as potentially lowering the noise due to the decreased gas velocity through the larger openings. As with previous embodiment the cross sectional areas of these flow paths can be modified to achieve the desired leak rate.

Figure 49:
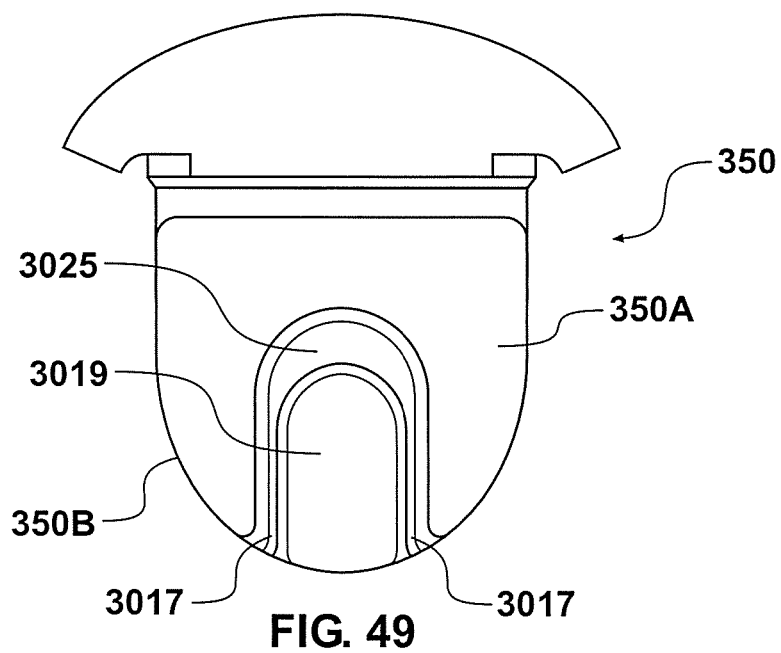
FIG. 49 is a plan view of a valve flap of another configuration of a conduit connector assembly in the form of an elbow assembly.
Figure 50:
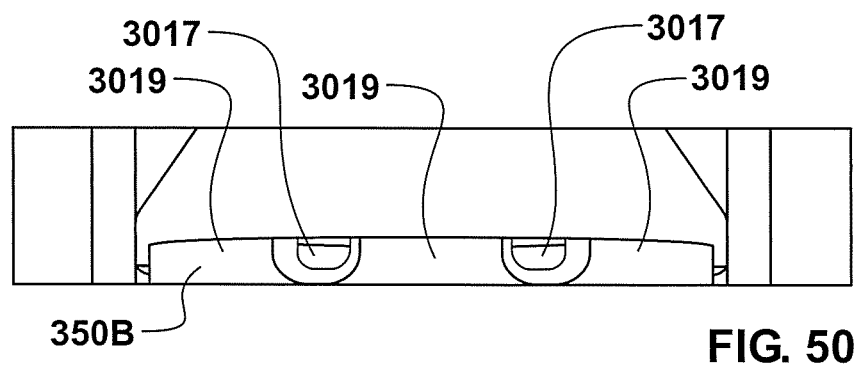
FIG. 50 is a front view of the valve flap of FIG. 49.

Referring now to FIGS. 49 and 50, the valve flap 350 is modified to comprise two medium-large slots 3017 with, for example, 0.3 mm radius fillets on all internal margins. The two slots 3017 fluidly couple an internal recessed region 3025 which is entirely contained within, and bounded by, the perimeter 350B of the valve flap 350. The two slots 3017 in combination with the internal recessed region 3025 form a substantially 'u' or 'n' shaped flow path when viewed from above.

Figure 51:
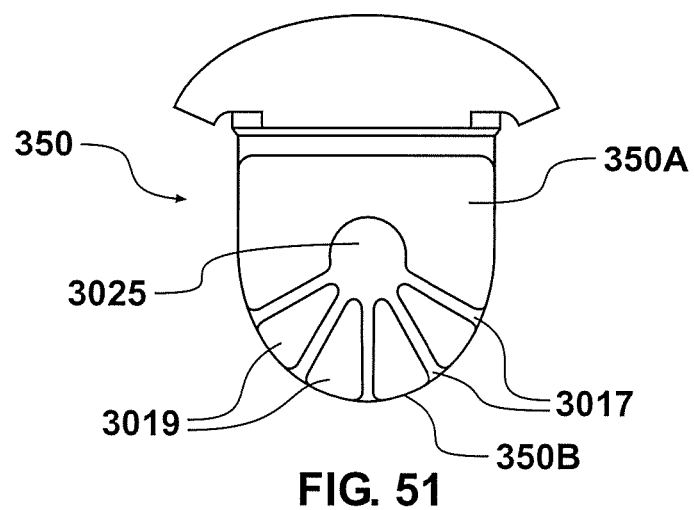
FIG. 51 is a plan view of a valve flap of another configuration of a conduit connector assembly in the form of an elbow assembly.
Figure 52:
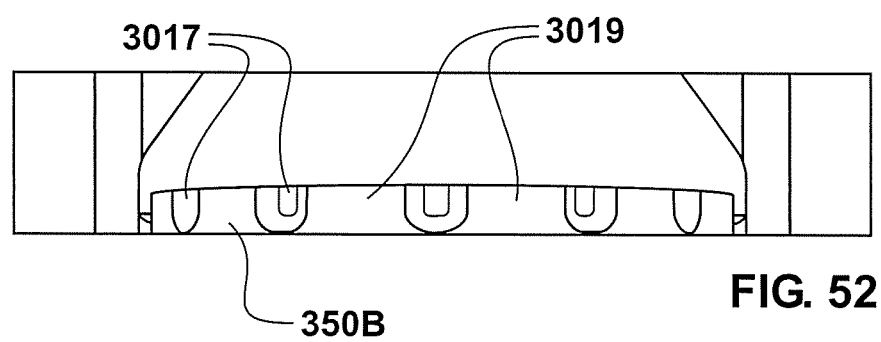
FIG. 52 is a front view of the valve flap of FIG. 51.

Referring now to FIGS. 51 and 52, the valve flap 350 is modified to comprise five slots 3017 with, for example, 0.3 mm radius fillets on all internal margins. The five slots 3017 fluidly couple an oval shaped internal recessed region 3025 with the perimeter of the flap 350. The flow path through the slots 3017 is generally longer than that of previous embodiments: this may reduce noise due to a more laminar flow being achieved. The increased length (when the flap 350 is viewed in plan, with the length of each slot 3017 being defined between adjacent pairs of the raised or castellated regions 3019) of the slots 3017 in combination with the reduced area of the recessed region 3025 helps maintain a relatively high level of rigidity in the flap 350 necessary to avoid the flap 350 collapsing in use.

Figure 53:
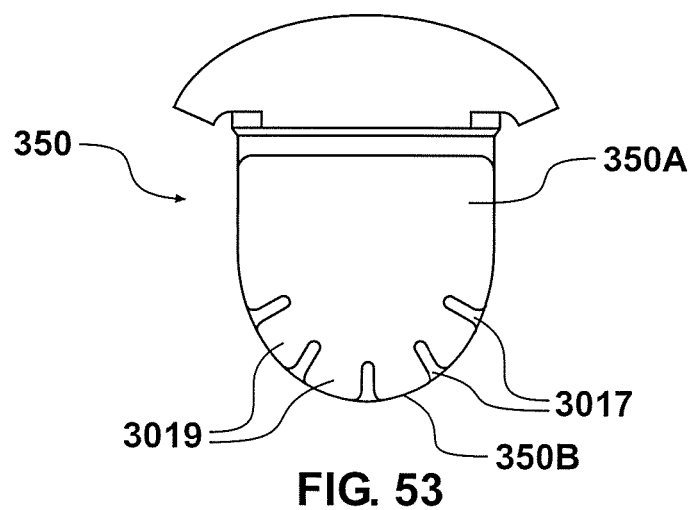
FIG. 53 is a plan view of a valve flap of another configuration of a conduit connector assembly in the form of an elbow assembly.
Figure 54:
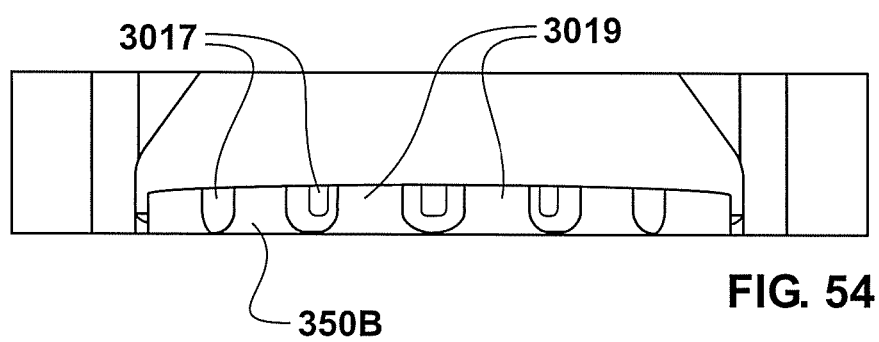
FIG. 54 is a front view of the valve flap of FIG. 53.

Referring now to FIGS. 53 and 54, the valve flap 350 is modified to comprise five slots 3017, and no recessed region(s). In this embodiment the flap 350 may be relatively stiff and resistant to deformation/collapse, with the length of the slots 3017 being selected to provide the required supplementary gas flow path, when the flap 350 abuts the elbow 222.

Figure 55:
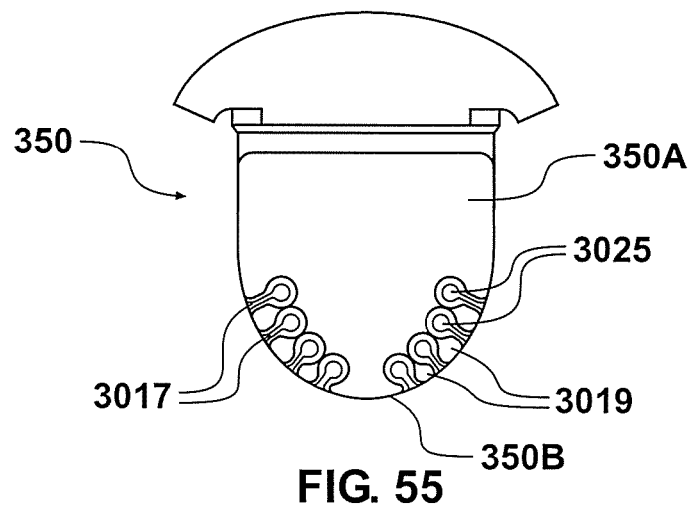
FIG. 55 is a plan view of a valve flap of another configuration of a conduit connector assembly in the form of an elbow assembly.
Figure 56:
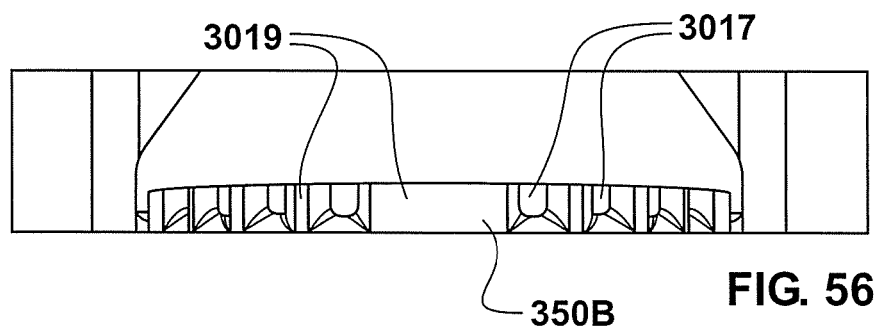
FIG. 56 is a front view of the valve flap of FIG. 55.

Referring now to FIGS. 55 and 56, the valve flap 350 is modified to comprise eight slots 3017 which each fluidly couple eight separate circular recessed regions 3025. The eight slots 3017 are separated into two groups of four, with each group being located offset from either side of the central axis of the flap 350, when viewed in plan (from above).

Figure 58:
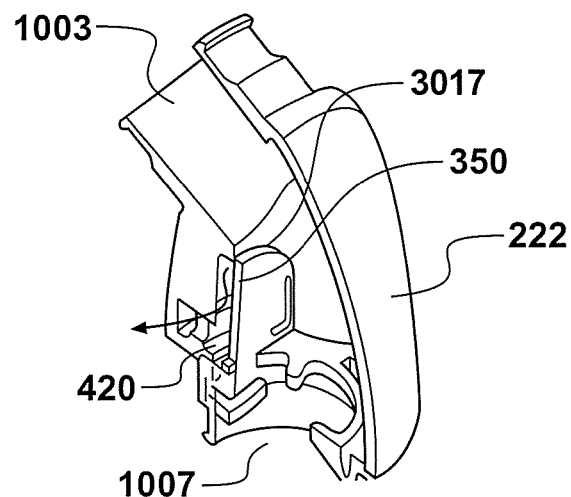
FIG. 58 is a cutaway perspective of the elbow assembly of FIG. 57 with the valve flap in a second position, showing the flow of gas through the assembly.
Figure 59:
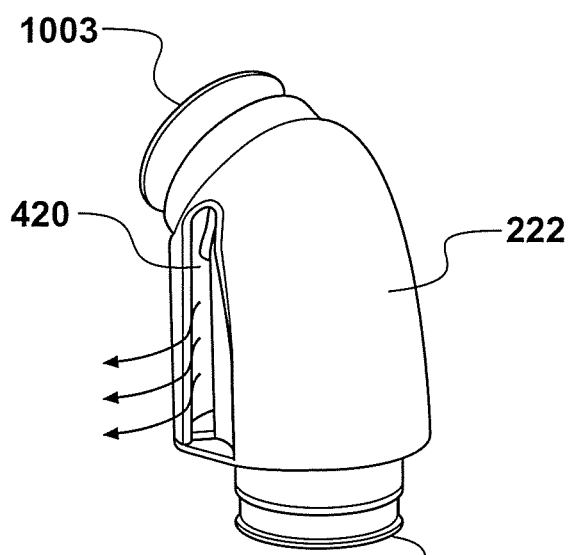
FIG. 59 is another perspective view of the elbow assembly of FIGS. 57 and 58, showing the flow of gas out of the assembly.

In these embodiments, the valve body 1017 is not required, and consequently second valve port 1021 and third valve port 1023 are not required. The elbow 222 is therefore substantially unmodified, with the valve flap 350 being movable between a first position, wherein the flap 350 at least partially blocks the part of the elbow 222 which is in fluid communication with the expiratory flow ports 420 and allows inspiratory gas from the gas delivery conduit to pass to a user via the elbow 222 while still allowing bias flow to be achieved through the intentional leak paths (shown by the arrows in FIGS. 58 and 59), and a second position, wherein the flap 350 at least partially blocks the gas delivery conduit thereby allowing expiratory gas to flow from the user to the expiratory flow ports 420. An example first position can be seen with reference to FIGS. 58 and 59, whilst an example second position can be seen with reference to FIG. 57.

The slots 3017 in the valve flap 350 form a supplementary gas flow path between the elbow flow channel 1009 and the expiratory flow ports 420. This supplementary gas flow path remains permanently open regardless of the position of the valve flap 350, and air to be expelled from flow channel 1009 through expiratory flow ports 420 during expiration. Thus the valve flap 350 forms part of the expiratory flow path when the system is pressurized, that is, when a pressurized flow of inspiratory gas enters elbow 222 via the gas delivery conduit A rigid component comprising the leak paths (slots, apertures, etc) could be overmoulded with silicone to create the valve flap 350. This could lead to an increased tolerance in the leak path dimensions as well as the leak path(s) not being deformed since the path(s) are created in a more rigid component or substrate.

In another embodiment the slots 3017 could be provided on the elbow 222, with the valve flap 350 not being provided with slots 3017. The international supplementary flow path would, as with the other described examples, be provide by a flow path defined between the elbow 222 and the sealing face of the valve flap 350.

It will be appreciated that whilst, for convenience, the above disclosure refers to an elbow assembly with non-aligned inlet and outlet ports, any aspect of this disclosure applies equally to any other configuration of conduit connector assembly comprising inlet and outlet ports configured to fluidly couple a patient interface with a breathing gas delivery conduit.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A conduit connector assembly for a respiratory therapy apparatus and configured to connect a patient interface to a gas delivery conduit, the conduit connector assembly comprising:
a conduit comprising a first flow port configured to be connected to the patient interface, and a second flow port configured to be connected to the gas delivery conduit, and a supplementary flow port configured to be in fluid communication with an ambient environment; and
a hollow valve body configured to be mounted on or in the conduit and comprising at least a first valve port positioned on the hollow valve body configured to be closed or opened by a valve flap, wherein the valve flap is configured to move between a first position and a second position relative to the hollow valve body;
the conduit, valve body and the valve flap being configured to selectively provide three flow paths through an elbow, being:
an therapy flow path provided between the second flow port of the conduit and the first flow port of the conduit;
an anti-asphyxiation flow path provided between the first flow port of the conduit and the supplementary flow port via the first valve port of the valve body, and wherein:
a supplementary gas flow path is provided between the first flow port and/or the second flow port and the supplementary flow port via a supplementary valve port of the valve body, and wherein the valve body and/or conduit is configured such that the supplementary gas flow path is permanently open.

2. The conduit connector assembly of claim 1 wherein the supplementary valve port is formed on a supplementary gas flow duct in communication with the valve body.

3. The conduit connector assembly of claim 2 wherein the supplementary gas flow duct projects from the valve body into the conduit.

4. The conduit connector assembly of claim 3 wherein the supplementary gas flow duct projects from the valve body to a position adjacent the first flow port of the conduit.

5. The conduit connector assembly of claim 3 wherein the supplementary gas flow duct projects from the valve body to a position projecting beyond the first flow port of the conduit, outside of the conduit.

6. The conduit connector assembly of claim 2 wherein the supplementary gas flow duct comprises a relatively short duct positioned inside the conduit and projecting into the conduit.

7. The conduit connector assembly of claim 6 wherein an end of the supplementary gas flow duct that projects into the conduit is closed by a duct end wall, the duct end wall being provided with at least one orifice configured to allow expiratory gas to flow from the conduit through the at least one orifice and into the supplementary gas flow duct.

8. The conduit connector assembly of claim 2 wherein the supplementary valve port is formed at one end of the supplementary gas flow duct distal from the valve body.

9. The conduit connector assembly of claim 2 wherein the supplementary gas flow duct comprises a relatively narrow diameter portion which extends from the valve body and along the conduit.

10. The conduit connector assembly of claim 2 wherein the supplementary valve port is defined in a relatively wide mouth portion of the supplementary gas flow duct, the relatively wide mouth portion being distal from the valve body.

11. The conduit connector assembly of claim 1 wherein the supplementary valve port is formed on the valve body.

12. The conduit connector assembly of claim 11 wherein the supplementary valve port comprises an array of valve ports formed on the valve body.

13. The conduit connector assembly of claim 1 wherein the valve body is elongate and comprises a first end face and a second end face, the first end face and the second end face comprising the first valve port and a second valve port respectively.

14. The conduit connector assembly of claim 13 wherein the first end face is planar along a first plane, with a second plane that is defined by the second end face is inclined relative to a longitudinal axis of the valve body.

15. A conduit connector assembly for a respiratory therapy apparatus and configured to connect a patient interface to a gas delivery conduit, the conduit connector assembly comprising:
a conduit comprising:
a first flow port configured to be connected to the patient interface,
a second flow port configured to be connected to the gas delivery conduit,
a supplementary flow port configured to be in fluid communication with an ambient environment; and
at least a first valve port configured to be closed or opened by a valve flap, wherein the valve flap is configured to move relative to the first valve port,
the conduit and the valve flap being configured to selectively provide three flow paths through the conduit, being:
an therapy flow path provided between the second flow port of the conduit and the first flow port of the conduit;
an anti-asphyxiation flow path provided between the first flow port of the conduit and the supplementary flow port via the first valve port, and wherein:
a supplementary gas flow path is provided between the first flow port and/or the second flow port and the supplementary flow port via a supplementary valve port defined by, or comprising part of:
the valve flap; or
the part of the conduit against which the valve flap seals when the valve flap provides the supplementary gas flow path, and wherein the valve flap or conduit is configured such that the supplementary gas flow path is permanently open.

16. The conduit connector assembly of claim 15 further comprising a gas flow directing structure that comprises a flow slot provided on or comprising part of the valve flap.

17. The conduit connector assembly of claim 16 wherein the flow slot extends from a position radially inward of a perimeter of the valve flap to a position at the perimeter of the valve flap, such that the supplementary gas flow path extends through the perimeter of the valve flap.

18. A conduit connector assembly for a respiratory therapy apparatus and configured to connect a patient interface to a gas delivery conduit, the conduit connector assembly comprising:

a conduit comprising a first flow port configured to be connected to the patient interface, and a second flow port configured to be connected to the gas delivery conduit, and a supplementary flow port configured to be in fluid communication with an ambient environment; and a first valve port configured to be closed or opened by a valve flap, wherein the valve flap is configured to move between a first position and a second position relative to the first valve port, the conduit and the valve flap being configured to selectively provide three flow paths through the conduit, being:

a therapy flow path between the second flow port of the conduit and the first flow port of the conduit;

an anti-asphyxiation flow path between the first flow port of the conduit and the supplementary flow port via the first valve port, and wherein:

a supplementary gas flow path is provided between the first flow port and/or the second flow port and the supplementary flow port via a supplementary valve port, and wherein the supplementary gas flow path is permanently open.

19. The conduit connector assembly of claim 18, wherein the supplementary valve port is provided on, or comprises part of:

the valve flap; or a hollow valve body configured to be mounted on or in the conduit.

* * * * *